United States Patent
Macak et al.

(10) Patent No.: US 12,285,317 B2
(45) Date of Patent: Apr. 29, 2025

(54) APPARATUSES, COMPUTER-IMPLEMENTED METHODS, AND COMPUTER PROGRAM PRODUCTS FOR MONITORING AUDIO PROTECTOR FIT

(71) Applicant: Honeywell Safety Products USA, Inc., Charlotte, NC (US)

(72) Inventors: Jaromir Macak, Brno (CZ); Charles Bondu, Brno (CZ); Sai Sreenivas Tekumalla, Secunderabad (IN); Marc Kirsch, Rock Hill, SC (US); Tomas Brhel, Brno (CZ); Alexander Kowolowski, Mosty u Jablunkova (CZ)

(73) Assignee: Honeywell Safety Products USA, Inc., Charlotte, NC (US)

( * ) Notice: Subject to any disclaimer, the term of this patent is extended or adjusted under 35 U.S.C. 154(b) by 269 days.

(21) Appl. No.: 17/812,562

(22) Filed: Jul. 14, 2022

(65) Prior Publication Data
US 2024/0016663 A1 Jan. 18, 2024

(51) Int. Cl.
*G08B 21/18* (2006.01)
*A61F 11/14* (2006.01)
(Continued)

(52) U.S. Cl.
CPC ............ *A61F 11/145* (2022.01); *G08B 21/18* (2013.01); *G10L 25/21* (2013.01); *H04R 1/1008* (2013.01);
(Continued)

(58) Field of Classification Search
CPC ....... A61F 11/145; G08B 21/18; G10L 25/21; H04R 1/1008; H04R 1/1041;
(Continued)

(56) References Cited

U.S. PATENT DOCUMENTS

| 11,115,750 B2 | 9/2021 | Monsarrat-Chanon et al. |
| 2015/0010158 A1* | 1/2015 | Broadley ................ A61F 11/14 381/58 |

(Continued)

OTHER PUBLICATIONS

Extended European Search Report Mailed on Nov. 24, 2023 for EP Application No. 23181666, 7 page(s).

(Continued)

*Primary Examiner* — Carolyn R Edwards
*Assistant Examiner* — Friedrich Fahnert
(74) *Attorney, Agent, or Firm* — Alston & Bird LLP

(57) ABSTRACT

Embodiments provide for improved determination of whether an audio protector is sufficiently fit to a wearer. By automatically performing the improved fit testing processes described, embodiments may warn users in circumstances where fit of their audio protector is dissatisfactory. Some embodiments include receiving external audio data and internal audio data including a filtered range of frequencies, generating comparative internal data by applying the internal audio data to an inverse attenuation model, identifying an audio processing mode based at least in part on the external audio data and/or the internal audio data, the audio processing mode associated with an audio comparison model, computing energy differential data by applying the comparative internal data and the external audio data to the audio comparison model; and determining a fit result based at least in part on the energy differential data.

19 Claims, 12 Drawing Sheets

(51) Int. Cl.
    *G10L 25/21*     (2013.01)
    *H04R 1/10*     (2006.01)
    *H04R 1/28*     (2006.01)
    *H04R 1/40*     (2006.01)
    *H04R 3/00*     (2006.01)
    *H04R 29/00*     (2006.01)

(52) U.S. Cl.
    CPC ......... *H04R 1/1041* (2013.01); *H04R 1/1075* (2013.01); *H04R 1/1083* (2013.01); *H04R 1/288* (2013.01); *H04R 1/406* (2013.01); *H04R 3/005* (2013.01); *H04R 29/001* (2013.01)

(58) Field of Classification Search
    CPC .... H04R 1/1075; H04R 1/1083; H04R 1/288; H04R 1/406; H04R 3/005; H04R 29/001; H04R 2460/15; H04R 29/00

USPC .......................................................... 381/21
See application file for complete search history.

(56) References Cited

U.S. PATENT DOCUMENTS

| | | |
|---|---|---|
| 2019/0075391 A1 | 3/2019 | Usher et al. |
| 2020/0107104 A1* | 4/2020 | Kim ..................... H04R 3/00 |
| 2020/0162808 A1 | 5/2020 | Monsarrat-Chanon et al. |
| 2020/0374622 A1* | 11/2020 | Kara ..................... A61F 11/14 |
| 2021/0176576 A1 | 6/2021 | Usher et al. |
| 2024/0130895 A1* | 4/2024 | Kvaløy ................. A61F 11/14 |

OTHER PUBLICATIONS

AU Notice of Allowance Mailed on Apr. 23, 2024 for AU Application No. 2023204012, 3 page(s).

* cited by examiner

APPARATUSES, COMPUTER-IMPLEMENTED METHODS, AND COMPUTER PROGRAM PRODUCTS FOR MONITORING AUDIO PROTECTOR FIT

TECHNICAL FIELD

Embodiments of the present disclosure generally relate to devices that protect from harmful audio levels, and specifically to devices and methodologies that detect whether a device for audio protection is properly fit.

BACKGROUND

In several contexts, a user will wear audio protection. Often, the user wears such audio protection to prevent loud audio from affecting the user. If the audio protection does not properly fit the user, however, the user may nevertheless may be exposed to harmful audio levels even while attempting to wear the audio protection. Often when using conventional audio protection, a user has no idea of whether the audio protection is sufficiently fit to the user until they are in a loud environment, and possibly already experiencing such harmful audio levels.

Applicant has discovered problems with current implementations of audio protection devices and with current implementations for determining appropriateness of a fit of an audio protection device for a user. Through applied effort, ingenuity, and innovation, Applicant has solved many of these identified problems by developing solutions embodied in the present disclosure, which are described in detail below.

BRIEF SUMMARY

In one aspect, a computer-implemented method includes receiving external audio data representing first energy associated with at least one first audio signal captured via the at least one external protector microphone of an audio protector, receiving internal audio data representing second energy associated with at least one second audio signal captured via at least one internal protector microphone of the audio protector, generating comparative external data by at least applying the external audio data to an inverse attenuation model, generating comparative internal data based at least in part on the internal audio data, identifying an audio processing mode based at least in part on the external audio data and/or the internal audio data, the audio processing mode associated with an audio comparison model, computing energy differential data by applying the comparative internal data and the comparative external data to the audio comparison model, and determining a fit result based at least in part on the energy differential data.

The computer-implemented method may further include where generating the comparative internal data further includes applying a first filtering model to the internal audio data, and where generating the comparative external data further includes applying a second filtering model to the external audio data.

The computer-implemented method may further include where the audio comparison model compares the comparative internal data and the comparative external data at each frequency band of a plurality of frequency bands.

The computer-implemented method may also further include, based at least in part on the comparison, causing outputting of a warning message via at least one output component associated with the audio protector.

The computer-implemented method may also further include setting a warning check timer based at least in part on the external audio data, and tracking a time since last check, where the remaining steps of the computer-implemented method are performed in a circumstance where the time since last check is determined to exceed the warning check timer.

The computer-implemented method may also further include outputting a warning message via at least one speaker of the audio protector.

The computer-implemented method may also further include outputting a warning message via at least one output component associated with the audio protector, where the warning message is output at a first rate in a circumstance where the energy associated with the at least one first audio signal is below a first energy threshold, and where the energy is output at a second rate in a circumstance where the energy associated with the at least one first audio signal is above the first energy threshold, where the second rate is faster than the first rate.

The computer-implemented method may also further include setting a warning check timer based at least in part on user interaction data, and tracking a time since last check, where the remaining steps of the computer-implemented method of claim 1 are performed in a circumstance where the time since last check is determined to exceed the warning check timer.

The computer-implemented method may also further include where receiving the external audio data includes capturing the at least one first audio signal via the at least one external protector microphone, and applying at least one audio filter to the at least one first audio signal to generate the data associated with the plurality of frequency ranges.

The computer-implemented method may also further include where receiving the internal audio data includes capturing the at least one second audio signal via the at least one internal protector microphone.

The computer-implemented method may also further include where the audio processing mode is selected from a plurality of candidate modes, the plurality of candidate modes includes a first mode selected in a circumstance where the external audio data and/or the internal audio data indicates a quiet level associated with the audio protector without user-generated audio, a second mode selected in a circumstance where the external audio data and/or the internal audio data indicates the quiet level associated with the audio protector with the user-generated audio, a third mode selected in a circumstance where the external audio data and/or the internal audio data indicates a moderately loud level associated with the audio protector without the user-generated audio, a fourth mode selected in a circumstance where the external audio data and/or the internal audio data indicates the moderately loud level associated with the audio protector with the user-generated audio, and a fifth mode selected in a circumstance where the external audio data and/or the internal audio data indicates a significantly loud level associated with the audio protector with or without the user-generated audio.

The computer-implemented method may also further include where identifying the audio processing mode based at least in part on the external audio data and/or the internal audio data includes determining an indication of user-generated audio in the external audio data and/or the internal audio data, and determining the audio processing mode based at least in part on the energy associated with the at least one first audio signal. Other technical features may be readily apparent to one skilled in the art from the following figures, descriptions, and claims.

The computer-implemented method may further include where generating the comparative internal data includes applying the internal audio data to an inverse hear-through model to generate updated internal audio data, and generating the comparative internal data based at least in part on the updated internal audio data. In some such embodiments, the compute-implemented method may further include where generating the comparative internal data based at least in part on the updated internal audio data includes applying the updated internal audio data to a filtering model to generate the comparative internal data.

In one aspect, an audio protector includes at least one external protector microphone positioned on an external portion of the audio protector. The audio protector also includes at least one internal protector microphone positioned on an internal portion of the audio protector. The audio protector also includes at least one sound dampener positioned between the external portion of the audio protector and the internal portion of the audio protector. The audio protector also includes at least one processor that is caused to receive external audio data representing first energy associated with at least one first audio signal captured via the at least one external protector microphone, receive internal audio data representing second energy associated with at least one second audio signal captured via the at least one internal protector microphone, generate comparative external data by at least applying the external audio data to an inverse attenuation model, generate comparative internal data based at least in part on the internal audio data, identify an audio processing mode based at least in part on the external audio data and/or the internal audio data, the audio processing mode associated with an audio comparison model, compute energy differential data by applying the comparative internal data and the comparative external data to the audio comparison model, and determine a fit result based at least in part on the energy differential data.

The audio protector may also further include at least one speaker, where the processor is further caused to at least based at least in part on the comparison, cause outputting of a warning message via the at least one speaker.

The audio protector may also further include at least one visual indicator, where the processor is further caused to at least based at least in part on the comparison, cause outputting of a warning message via the at least one visual indicator.

The audio protector may also further include the processor further configured to select the audio processing mode is selected from a plurality of candidate modes, the plurality of candidate modes includes a first mode selected in a circumstance where the external audio data and/or the internal audio data indicates a quiet level associated with the audio protector without user-generated audio, a second mode selected in a circumstance where the external audio data and/or the internal audio data indicates the quiet level associated with the audio protector with the user-generated audio, a third mode selected in a circumstance where the external audio data and/or the internal audio data indicates a moderately loud level associated with the audio protector without the user-generated audio, a fourth mode selected in a circumstance where the external audio data and/or the internal audio data indicates the moderately loud level associated with the audio protector with the user-generated audio, and a fifth mode selected in a circumstance where the external audio data and/or the internal audio data indicates a significantly loud level associated with the audio protector with or without the user-generated audio.

The audio protector may also further include where the processor is caused to capture the at least one first audio signal via the at least one external protector microphone, and capture the at least one second audio signal via the at least one internal protector microphone.

The audio protector may also further include where the processor is further caused to select, based at least in part on user interaction data, a selected mode from a plurality of modes.

The audio protector may also further include where the processor is further caused to set a warning check timer based at least in part on the external audio data, and track a time since last check, where the processor is further caused to perform the remaining operations in a circumstance where the time since last check is determined to exceed the warning check timer. Other technical features may be readily apparent to one skilled in the art from the following figures, descriptions, and claims.

The audio protector may also further include where to generate the comparative internal data the processor is caused to apply the internal audio data to an inverse hear-through model to generate updated internal audio data, and generate the comparative internal data based at least in part on the updated internal audio data. In some such embodiments, the audio protector may further include where to generate the comparative internal data based at least in part on the updated internal audio data the processor is caused to apply the updated internal audio data to a filtering model to generate the comparative internal data.

In one aspect, a computer program product includes at least one non-transitory computer-readable storage medium having computer program code stored thereon that, in execution with at least one processor configure the computer program product for receiving external audio data representing first energy associated with at least one first audio signal captured via the at least one external protector microphone of an audio protector, receiving internal audio data representing second energy associated with at least one second audio signal captured via at least one internal protector microphone of the audio protector, generating comparative external data by at least applying the external audio data to an inverse attenuation model, generating comparative internal data based at least in part on the internal audio data, identifying an audio processing mode based at least in part on the external audio data and/or the internal audio data, the audio processing mode associated with an audio comparison model, computing energy differential data by applying the comparative internal data and the comparative external data to the audio comparison model, and determining a fit result based at least in part on the energy differential data.

The computer program product may also further include where identifying the audio processing mode based at least in part on the external audio data and/or the internal audio data includes determining an indication of user-generated audio in the external audio data and/or the internal audio data, and determining the audio processing mode based at least in part on the energy associated with the at least one first audio signal.

The computer program product may also further include where the audio processing mode is selected from a plurality of candidate modes, the plurality of candidate modes includes a first mode selected in a circumstance where the external audio data and/or the internal audio data indicates a quiet level associated with the audio protector without user-generated audio, a second mode selected in a circumstance where the external audio data and/or the internal audio data indicates the quiet level associated with the audio protector with the user-generated audio, a third mode selected in a circumstance where the external audio data and/or the internal audio data indicates a moderately loud level associated with the audio protector without the user-generated audio, a fourth mode selected in a circumstance where the external audio data and/or the internal audio data indicates the moderately loud level associated with the audio protector with the user-generated audio, and a fifth mode selected in a circumstance where the external audio data and/or the internal audio data indicates a significantly loud level associated with the audio protector with or without the user-generated audio. Other technical features may be readily apparent to one skilled in the art from the following figures, descriptions, and claims.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
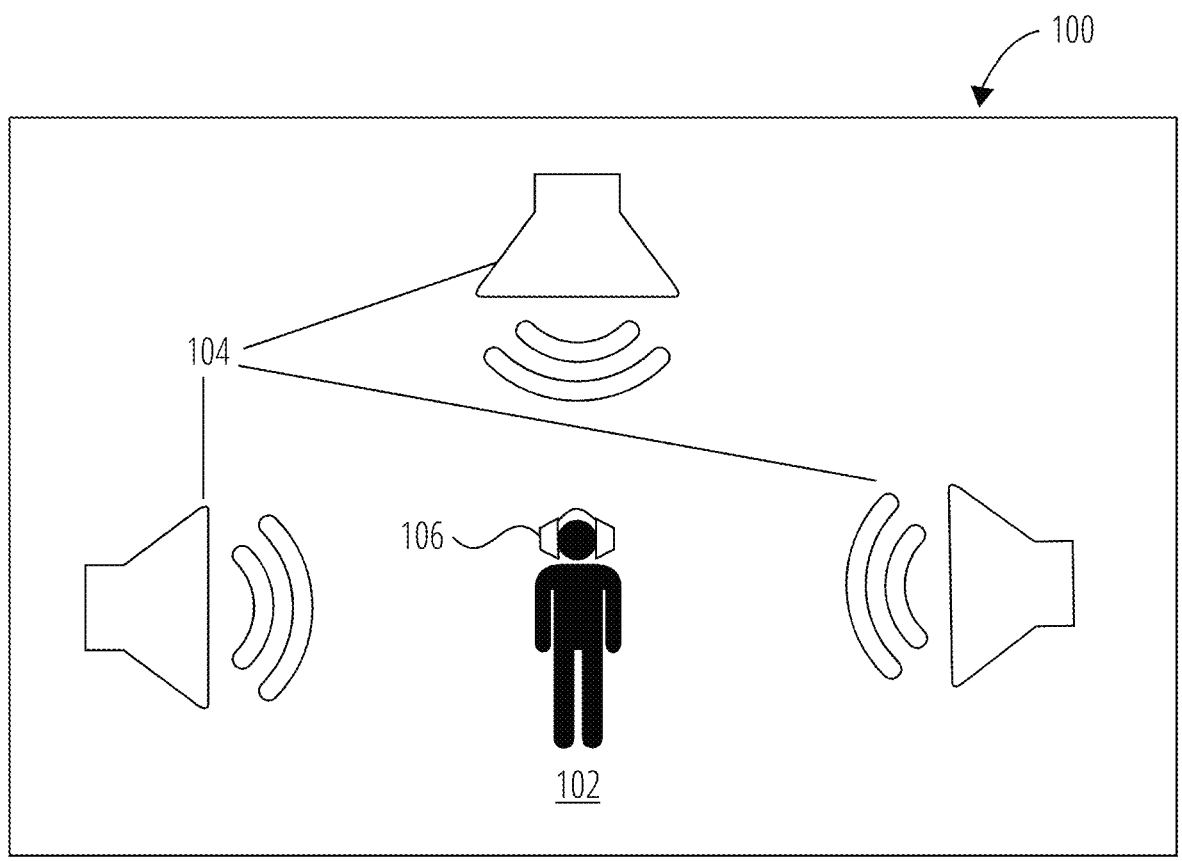
FIG. 1 illustrates an example environment including a user using an audio protector in accordance with at least one embodiment of the present disclosure.

Embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

OVERVIEW

In several contexts a user risks being exposed to loud sounds that could negatively impact the user's hearing. For example, in one example context a user in a factory workspace may be exposed to machinery sounds during a working period, with such sound exposure causing harm to the user's hearing. Harm to the user's hearing may be caused by the effects of audio signals impacting the user's ear canals (e.g., vibrations caused by the energy of such audio signals). Attenuation of such audio signals is ideal to reduce the negative effects of such audio signals as they impact the user.

Often, a user may utilize audio protection to attenuate audio signals from the environment before such signals impact the user. For example, a user may utilize over-the-ear headphones/earmuffs or in-ear earplugs to attenuate the audio signals that reduce the energy of such audio signals before the signals reach the ear canal. A given piece of audio protection, however, may fit each user differently. Even though a user may utilize a particular piece of audio protection, a poor fit of such audio protection may nevertheless pose a risk to harming the user by failing to sufficiently attenuate audio signals from the environment. While a user may strive to prevent use of poorly fitting audio protection, a user often lacks sufficient methodologies to determine whether a given piece of audio protection is sufficiently protecting the user whilst the audio protection is being worn.

Embodiments of the present disclosure provide improved audio protectors and methodologies for fit testing such audio protectors. Some embodiments include audio protectors that include external protector microphone(s) and internal protector microphone(s). External audio data and internal audio data are generated from the audio signals captured by such external protector microphone(s) and internal protector microphone(s) respectively, and are processed to determine whether the audio protector first a wearer in a manner that sufficiently attenuates audio signals before they reach an internal portion of the audio protector. The portions of audio data may be processed utilizing one or more models, for example at least one audio comparison model. In a circumstance where the audio data is determined to indicate that the audio protector is insufficiently attenuating the audio signals in the environment (e.g., energy differential data determined based on the internal audio data and external audio data satisfies a warning threshold), at least one warning message may be generated and/or output to indicate to a user that the audio protector is not sufficiently fitting the user. In this regard, such embodiments can automatically and continuously monitor such circumstances for a given user, and warn the user to prevent or minimize harm to the user's hearing.

Additionally or alternatively, embodiments of the present disclosure utilize one or more model(s) that enable accurate determination of whether an audio protector sufficiently fits in environments of various sound levels. In some embodiments a mode is identifiable based on the energy level for current audio signals captured from an environment. In this regard, a particular model corresponding to the particular mode may be selected from a plurality of models. Each model may be specially configured to function in different environments (e.g., very loud environments, loud environments, and quiet environments) and/or using different types of audio signals (e.g., environment signals as opposed to user-generated audio). Accordingly, some embodiments of the present disclosure advantageously provide accurate determinations in each of such environments and circumstances. Additionally or alternatively, some embodiments of the present disclosure advantageously automatically determine and may switch between modes to ensure that the appropriate mode is selected for accurate use in the user's current environment.

Definitions

"Audio comparison model" refers to one or more algorithmic, statistical, and/or machine-learning model that compares two or more portions of audio data. In some embodiments, an audio comparison model determines a difference between the energy associated with two portions of audio data.

"Audio data" refers to electronically managed data representing one or more measurable characteristics of audio signals captured and/or otherwise received via one or more device(s). In some contexts the audio data is converted from an audio signal utilizing an analog-to-digital converter. In some embodiments, audio data includes at least, and without limitation, data representing an energy/decibel level, a frequency bandwidth, a voltage level, and/or another property utilized to characterize one or more aspects of an audio signal.

"Audio filter" refers to one or more device(s) embodied in hardware, software, firmware, and/or a combination thereof, that segments an audio signal based at least in part on frequency bounds. In some embodiments, one or more audio filter(s) segments audio signal(s) into a low frequency group below a particular frequency threshold, and a high frequency group above the particular frequency threshold.

"Audio processing mode" and "mode" refer to electronically managed data representing an indication of a state of operation to be utilized in processing one or more portions of audio data. In some embodiments, an audio processing mode is associated with data linking the audio processing mode to a corresponding audio comparison model to be used to process audio data in a circumstance where a device is operating in the audio processing mode.

"Audio protector" refers to a device that dampens, attenuates, and/or otherwise diminishes the energy level of audio vibrations on a user when the user is wearing or otherwise operating utilizing the audio protector. Non-limiting examples of an audio protector include in-ear plugs, over-the-ear headphones, and connected earmuffs.

"Audio signal" refers to electrical signals output via a microphone that represent one or more aspects of audio captured via the microphone.

"Comparative internal data" refers to modified, filtered, or otherwise processed internal audio data to be compared to one or more other portion(s) of audio data. In some embodiments, comparative internal data includes a version of internal audio data processed via one or more algorithms for comparison with corresponding external audio data and/or data derived therefrom.

"Comparative external data" refers to modified, filtered, or otherwise processed external audio data to be compared to one or more other portion(s) of audio data. In some embodiments, comparative external data includes a version of external audio data processed via one or more algorithm(s) for comparison with corresponding internal audio data and/or data derived therefrom. In some embodiments, comparative external data is generated based at least in part via an inverse attenuation model.

"Energy differential data" refers to electronically managed data representing a value indicative of a difference in energy levels between two portion(s) of audio data. In one example context, energy differential data representing a value of 0 indicates a real attenuation of an audio data matches an expected attenuation of said audio data.

"External audio data" refers to electronically managed data representing audio signal(s) captured via at least one external protector microphone. External audio data represents such audio signal(s) associated with the external environment surrounding an audio protector.

"External portion of the audio protector" refers to at least a portion of the audio protector that is exposed to an environment without attenuation of one or more sound dampening elements of the audio protector. In a context where the audio protector embodies over the ear cuffs for example, the external portion of the audio protector includes the portion of each ear cuff that is exposed to the environment while the user is wearing the audio protector. In a context where the audio protector embodies an in-ear plug, the external portion of the audio protector includes the portion of the in-ear plug that does not rest in the wearer's ear canal.

"External protector microphone" refers to a microphone that captures audio signals from an environment before attenuation by one or more dampeners of the audio protector. In some embodiments an external protector microphone is positioned along an external portion of an audio protector.

"Frequency range" refers to a plurality of frequencies spanning between a lower frequency and a higher frequency.

"Internal audio data" refers to electronically managed data representing audio signal(s) captured via at least one internal protector microphone. Internal audio data represents such audio signal(s) associated with an internal portion of the audio protector.

"Internal portion of the audio protector" refers to at least a portion of the audio protector that is positioned past one or more dampener(s) while a user is wearing the audio protector, such that the dampener(s) attenuate audio signals before they reach the user. In a context where the audio protector embodies over the ear cuffs for example, the internal portion of the audio protector includes the internal portion of each ear cuff that is past one or more dampener(s) that surround the user's ear while the user is wearing the audio protector. In a context where the audio protector embodies an in-ear plug, the internal portion of the audio protector includes the portion of the in-ear plug that rests in the wearer's ear canal.

"Internal protector microphone" refers to a microphone that captures audio signals after attenuation by one or more dampeners of an audio protector. In some embodiments an internal protector microphone is positioned along an internal portion of the audio protector.

"Inverse attenuation model" refers to one or more algorithmic, statistical, and/or machine learning model(s) that approximate reversal of attenuation by one or more dampener(s) that affected an audio signal. In one example context the inverse attenuation model is embodied by one or more equalizer filter(s).

"Mode" refers to electronically managed data having a value that controls at least one operational aspect of a computing program. In some embodiments, a mode embodies a data value that is utilized by a computing program for one or more determination(s), to initiate one or more particular process(es), and/or to specify a particular model or algorithm to utilize for processing data.

"Moderately loud level" refers to data signal(s) associated with at least one data value(s) indicating a loudness level where the data value(s) fall between a lower threshold level and an upper threshold level.

"Output component" refers to hardware, software, firmware, and/or any combination thereof that produces signal(s) perceptible by a user utilizing one or more of the user's senses. Non-limiting examples of an output component include at least one speaker, at least one light indicator, a touchscreen display, and a monitor display.

"Quiet level" refers to refers to data signal(s) associated with at least one data value(s) indicating a loudness level where the data value(s) fall under a lower threshold level.

"Significantly loud level" refers to data signal(s) associated with at least one data value(s) indicating a loudness level where the data value(s) exceed above an upper threshold level.

"Sound dampener" and "dampener" refers to physical component(s) intended to attenuate audio signal(s) that engage or otherwise interact with the sound dampener.

"Time since last check" refers to electronically managed data that represents a time interval since a previous timestamp at which a process was initiated or completed.

"User interaction data" refers to electronically managed data representing any engagement with a device. Non-limiting examples of user interact data include touch data, gesture data, voice command data, motion data, peripheral input data, and video input data.

"User-generated audio" refers to electronically managed data representing audio signals generated by a user. Non-limiting examples of user-generated audio includes electronically managed data representing a recording of a user's voice, breathing sounds, cough, chewing, and other bodily sound.

"Visual indicator" refers to any hardware, software, firmware, and/or combination thereof, that is usable to visually depict data value(s) to a user. Non-limiting examples of a visual indicator include at least one specially configurable light, a high-definition display, and a touchscreen display.

"Warning check timer" refers to electronically managed data representing a threshold timestamp interval after which a process for performing an audio fit test is to be performed.

"Warning message" refers to electronically managed data outputted via one or more output component associated with an audio protector, wherein the data is utilized to indicate a warning that the audio protector should be adjusted.

"Warning threshold" refers to electronically managed data representing a threshold for a differential in energy between two audio signals that, if exceeded, indicates a warning should be output. A warning threshold may be dynamically determined, set by a user, or set via at least one setting.

Example Environments and Apparatuses of the Disclosure

FIG. 1 illustrates an example environment including a user using an audio protector in accordance with at least one embodiment of the present disclosure. Specifically, FIG. 1 depicts an example environment 100. The environment 100 includes a user 102 and audio source(s) 104. It will be appreciated that the environment 100 embodies an example environment and in other contexts, one or more aspects of the environment may differ. For example, in some contexts the environment includes a plurality of users, more audio sources, or no audio sources external from the user 102. In one example context, the user 102 may be in a quiet environment having no external audio sources at all, such that user-generated audio is utilized to perform he applicable audio fit test.

The environment 100 includes a user 102. The user 102 may embody a human user in the particular environment, for example a worker in a workspace, factory, or the like. The user 102 is wearing an audio protector 106, for example depicted as over-the-ear headphones that cover both ears of the user 102. In some embodiments, the audio protector 106 embodies a fit testing audio protector as described herein. As the audio protector 106 may fit the user 102 differently for any of a myriad of reasons (e.g., due to glasses or other items worn by the user 102, based on a size or configuration of the audio protector 106, and/or the like), testing the fit of the audio protector 106 advantageously enables determination of whether the fit of the audio protector 106 is sufficient (e.g., attenuating audio signal energy by a particular amount). In a circumstance where the audio protector 106 is not sufficiently fit to the user, the audio protector 106 may initiate outputting of a warning message to the user 102 regarding adjusting of the audio protector 106, replacement of the audio protector 106, and/or the like. An example embodiment of the audio protector 106 is depicted and described herein with respect to the audio protector 200 in FIG. 2.

Optionally, in some embodiments the environment 100 includes one or more audio source(s) 104. The audio source(s) 104 may include any of a myriad of sound-producing device(s), system(s), component(s), machinery, and/or the like. For example, in some contexts, the audio source(s) 104 include one or more speaker(s) or other digital sound-producing device(s) that product audio signal(s) at particular volumes/energy level(s). In other contexts, the audio source(s) 104 includes machinery that produces audio signals during operation.

The audio source(s) 104 may each produce audio signals throughout the environment 100. In this regard, the audio signals may flow through the environment and impact the user 102. The user 102 may utilize the audio protector 106 to reduce the impact of the audio signals on the user's hearing (e.g., by attenuating the audio signals before they impact the ears of the user 102). In this regard, in circumstances where the audio source(s) 104 are present and generating audio signals external to the user 102, such audio signals may be captured and processed to determine a fit for the audio protector 106 on the user 102.

In some contexts, the environment 100 does not include any audio source(s) 104 external from the user 102, or the audio source(s) 104 do not produce any audio signals or audio signals of sufficient energy for detection by microphones of the audio protector 106. In some such embodiments, the user 102 may produce user-generated audio signals that are capturable by the microphones of the audio protector 106. In this regard, such user-generated audio signals are processable in lieu of environmental audio to perform a fit test algorithm in such circumstances where the user is in a quiet environment. Accordingly, the audio protector 106 may advantageously be configured to perform in different modes that accurately process the particular audio signals captured and accurately performs in environments of various loudness, as described further herein.

Figure 2:
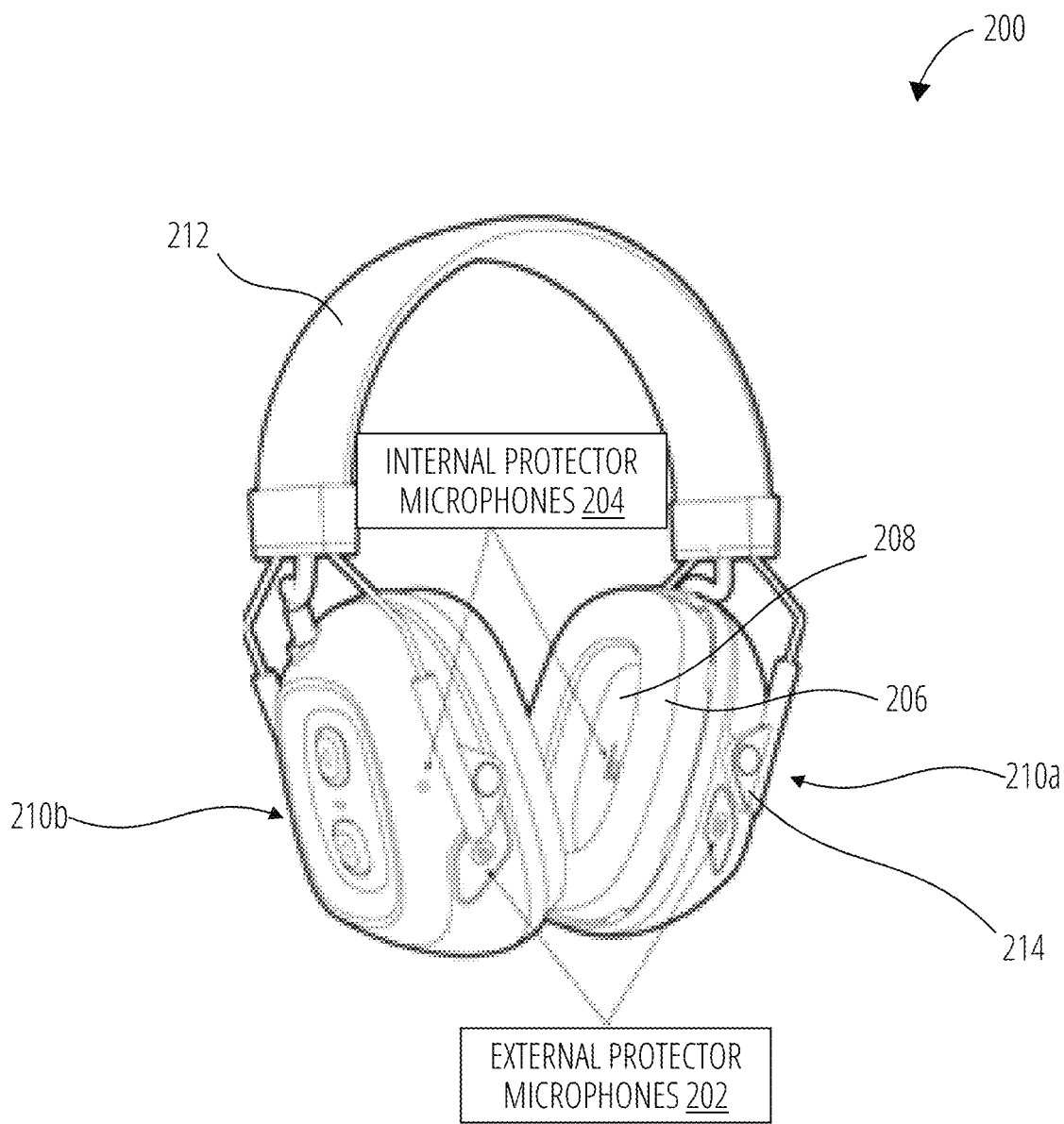
FIG. 2 illustrates an example audio protector in accordance with at least one embodiment of the present disclosure.

FIG. 2 illustrates an example audio protector in accordance with at least one embodiment of the present disclosure. Specifically, FIG. 2 depicts an example fit testing audio protector embodied as audio protector 200. The fit testing audio protector is specially configured to enable capturing of audio signals from an environment, and processing of the captured audio signals to determine whether the audio protector sufficiently fits a user wearing said audio protector. In this regard, the audio protector 200 may perform such a fit test to determine whether the audio protector 200 is sufficiently fit to a user, and generate or otherwise output a warning message in a circumstance where audio protector 200 determines that such a fit is insufficient, for example based on energy differential data as described herein.

The audio protector 200 includes a left ear cup and a right ear cup, specifically ear cup 210a and ear cup 210b respectively. Each ear cup receives a user's ear on an internal portion, such that a sound dampener is positioned between the user's ear and the rest of the environment. In this regard, the sound dampener separates the user's ear from the environment, attenuating audio signals before they reach the user's ear. In some embodiments, the ear cup 210a and ear cup 210b are connected via a cup connector 212. In this regard, the cup connector 212 affixes the ear cups 210a and 210b at a fixed or relatively fixed distance, for example to enable the user to fit their head between the ear cups 210a and 210b.

Each ear cup includes an external portion and an internal portion. Specifically, the ear cup 210a includes an internal portion of the audio protector 208 and an external portion of the audio protector 214. The external portion of the audio protector 214 is exposed to the environment, including any audio signals flowing in the environment before such audio signals are attenuated by any sound dampener of the audio protector 200. Alternatively, the internal portion of the audio protector 208 may be defined by the inner volume surrounded by one or more sound dampener(s), such as the sound dampener 206. In this regard, as the user may position their ear in or on the internal portion of the audio protector 208, with the sound dampener 206 around and/or on the user's ear to attenuate audio signal(s) before they reach the user's ear. In this regard, the audio signals that reach the external portion of the audio protector 214 may differ in energy level from the energy level of audio signals that reach the internal portion of the audio protector 208 after attenuation by the sound dampener 206.

Each ear cup includes a sound dampener, such as the sound dampener 206. In some embodiments, the sound dampener 206 is embodied by a leather, foam, vinyl, thermoplastic, or other material surround intended to rest on a user's ear or around a user's ear. In this regard, as audio signals from the environment impact the sound dampener 206, the sound dampener 206 attenuates such audio signals before they reach the user's ear while the audio protector 200 is positioned on the user. It will be appreciated that based on any of a myriad of factors (e.g., glasses suspending at least a portion of the sound dampener 206 from the user's head and/or ear, poorly fitting sound dampeners 206 and/or poor orientation of the audio protector 200 that leave gap(s) between the sound dampener 206 and the user's head, and/or the like). In this regard, in a circumstance where a user positions the audio protector 200 such that the ear cups 210a and 210b are positioned around the user's ears, the sound dampeners 206 reduce the energy levels of the audio signals to reduce any harm such audio signals may have on the user's hearing. In some embodiments, the sound dampener 206 is expected or otherwise associated with a particular decrease in energy level of the audio signals, for example based on the attenuation specific to the material, design, and/or other configuration of the sound dampener 206.

In some embodiments, a level of attenuation caused by the sound dampener 206 is determinable or predetermined based on previous testing of the audio protector 200. For example, energy differential data indicating a drop in energy level measured from signals captured via the external protector microphones 202 to signals captured via the internal protector microphones 204 may be measured in circumstances where an audio protector 200 is determined to be worn by a user with an accurate fit. In this regard, the measured energy differential data may be stored as the expected energy differential data in a circumstance where a user has a good fit. Such a stored energy differential data may embody a reference data to be compared to energy differential data during a subsequent fit testing process, as described further herein.

The audio protector 200 further includes external protector microphones 202 and internal protector microphones 204. Specifically, the external protector microphones 202 are positioned or otherwise exposed along the external portion of the audio protector 214. Similarly, the internal protector microphones 204 are positioned or otherwise exposed along the internal portion of the audio protector 208. In this regard, the external protector microphones 202 may capture audio signals from the environment surrounding the audio protector 200 (e.g., which have not been attenuated by the audio protector 200), while the internal protector microphones 204 may capture audio signals after attenuation via the components of the audio protector 200 (e.g., via the sound dampener 206 on each ear cup).

It will be appreciated that in other embodiments, the audio protector 200 need not be the specific around-the-ear configuration as depicted. For example, in some embodiments the audio protector 200 includes only a single ear cup. In some embodiments, the audio protector 200 embodies a dual-cup over-the-ear configuration designed such that the internal portion of the audio protector rests on the user's ear rather than around the ear. Alternatively or additionally still, in some embodiments, the audio protector 200 embodies an in-ear protector having an internal portion of the audio protector within the user's ear canal. In any such implementation(s), the fit testing processes and model(s) may function the same as depicted and described herein.

Figure 3:
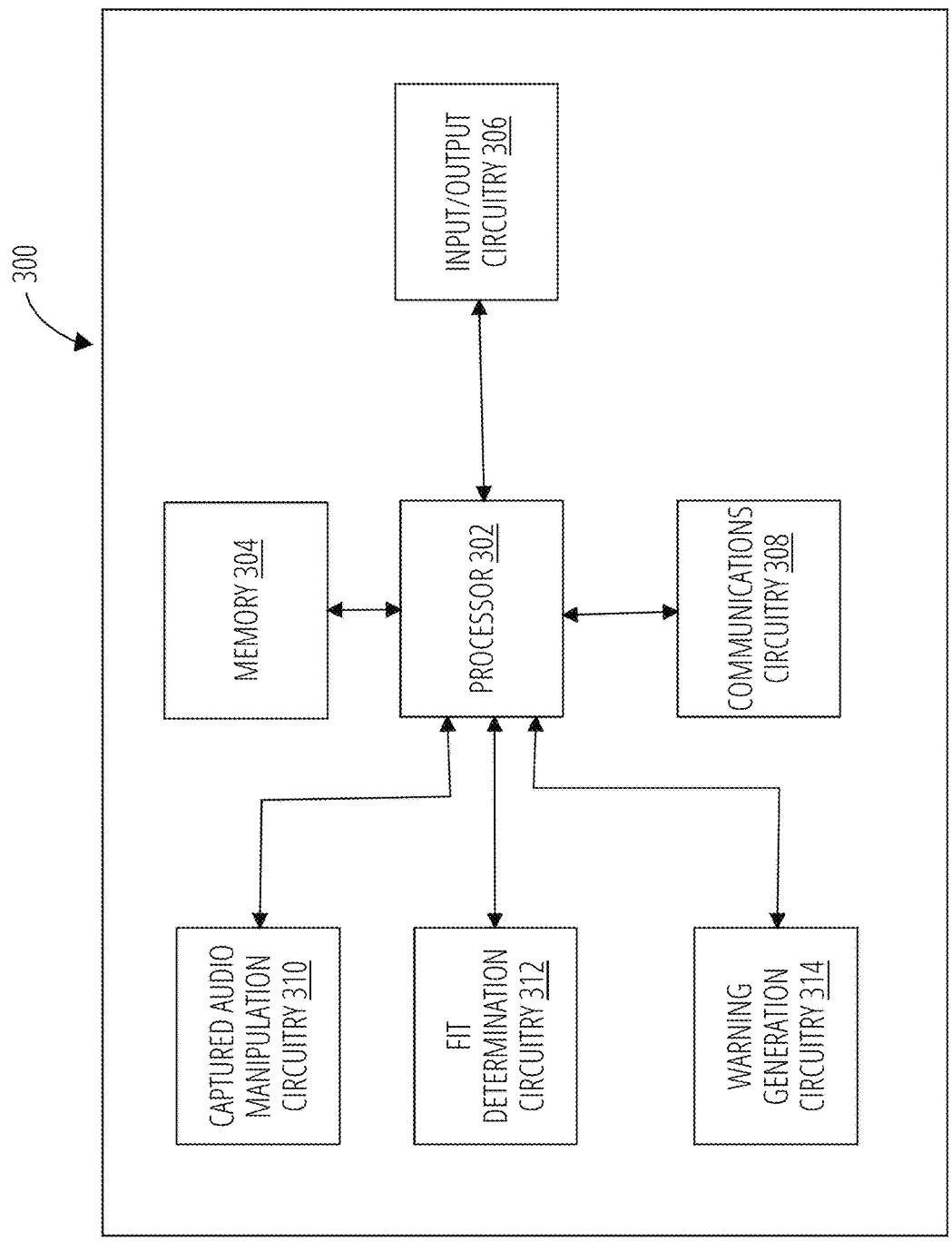
FIG. 3 illustrates an example apparatus for fit testing in accordance with at least one embodiment of the present disclosure.

FIG. 3 illustrates an example apparatus for fit testing in accordance with at least one embodiment of the present disclosure. In some embodiments, the audio protector 106 (and/or audio protector 200) is embodied by one or more specially configured computing device(s), such as the apparatus 300 as depicted and described in FIG. 3. The apparatus 300 may include one or more dampening element(s), physical components that construct a particular shape, design and/or configuration for audio protection (e.g., as depicted and described with respect to FIG. 2), and computing device(s) embodied in hardware, software, firmware, and/or a combination thereof that performs any of a myriad of operations for fit testing as described herein. Alternatively or additionally, in some embodiments, the apparatus 300 embodies a specially configured computing device that performs an audio fit test based on data received associated with a particular audio protector. For example, in some embodiments, the apparatus 300 embodies a user device, server, central terminal, personal computer, or other one or more computing device(s) external to an audio protector that receives data captured by internal and external protector microphones of a particular audio protector, and processes such data to determine whether the data indicates a satisfactory fit of the audio protector on a particular wearer.

The apparatus 300 includes a processor 302, memory 304, input/output circuitry 306, communications circuitry 308, captured audio manipulation circuitry 310, fit determination circuitry 312, and warning generation circuitry 314. In some embodiments, the apparatus 300 is configured, using one or more of the sets of circuitry 302, 304, 306, 308, 310, 312, and/or 314, to execute the operations of the various functions described with respect to the audio protector 106 and/or 200 and further herein. In some embodiments, one or more of the circuitry portions are embodied in an external device communicable with the apparatus 300. For example, in some embodiments, the apparatus 300 communicates with an external user device, warning system, and/or the like.

Although components are described with respect to functional limitations, it should be understood that the particular implementations necessarily include the use of particular computing hardware. It should also be understood that in some embodiments, certain of the components described herein include similar or common hardware. For example, two sets of circuitry may both leverage use of the same processor(s), network interface(s), storage medium(s), and/or the like, to perform their associated functions, such that duplicate hardware is not required for each set of circuitry. The use of the term "circuitry" as used herein with respect to the components of the apparatus(es) described herein should therefore be understood to include particular hardware configured, for example via software and/or firmware, to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Alternatively or additionally, in some embodiments, other elements of the apparatus 300 provide or supplement the functionality of other particular sets of circuitry. For example, the processor 302 in some embodiments provides processing functionality to any of the sets of circuitry, the memory 304 provides storage functionality to any of the sets of circuitry, the communications circuitry 308 provides network interface functionality to any of the sets of circuitry and/or external device(s), and/or the like.

In some embodiments, the processor 302 (and/or co-processor or any other processing circuitry assisting or otherwise associated with the processor) is/are in communication with the memory 304 via a bus for passing information among components of the apparatus 300. In some embodiments, for example, the memory 304 is non-transitory and may include, for example, one or more volatile and/or non-volatile memories. In other words, for example, the memory 304 in some embodiments includes or embodies an electronic storage device (e.g., a computer readable storage medium). In some embodiments, the memory 304 is configured to store information, data, content, applications, instructions, or the like, for enabling the apparatus 300 to carry out various functions in accordance with example embodiments of the present disclosure.

The processor 302 may be embodied in a number of different ways. For example, in some example embodiments, the processor 302 includes one or more processing devices configured to perform independently. Additionally or alternatively, in some embodiments, the processor 302 includes one or more processor(s) configured in tandem via a bus to enable independent execution of instructions, pipelining, and/or multithreading. The use of the terms "processor" and "processing circuitry" should be understood to include a single core processor, a multi-core processor, multiple processors internal to the apparatus 300, and/or one or more remote or "cloud" processor(s) external to the apparatus 300.

In an example embodiment, the processor 302 is configured to execute instructions stored in the memory 304 or otherwise accessible to the processor. Alternatively or additionally, the processor 302 in some embodiments is configured to execute hard-coded functionality. As such, whether configured by hardware or software methods, or by a combination thereof, the processor 302 represents an entity (e.g., physically embodied in circuitry) capable of performing operations according to an embodiment of the present disclosure while configured accordingly. Alternatively or additionally, as another example in some example embodiments, when the processor 302 is embodied as an executor of software instructions, the instructions specifically configure the processor 302 to perform the algorithms embodied in the specific operations described herein when such instructions are executed.

As one particular example embodiment, the processor 302 is configured to perform various operations associated with automatic audio fit testing. In some embodiments, the processor 302 includes hardware, software, firmware, and/or a combination thereof, that receives and/or otherwise captures external audio data. Additionally or alternatively, in some embodiments, the processor 302 includes hardware, software, firmware, and/or the like, that receives internal audio data. Additionally or alternatively, in some embodiments, the processor 302 includes hardware, software, firmware, and/or the like, that generates comparative internal data and/or comparative external data. Additionally or alternatively, in some embodiments, the processor 302 includes hardware, software, firmware, and/or the like, that identifies an audio processing mode corresponding to an audio comparison model. Additionally or alternatively, in some embodiments, the processor 302 includes hardware, software, firmware, and/or the like, that computes energy differential data and determines whether the energy differential data indicates a satisfactory fit or a dissatisfactory fit. It will be appreciated that a determination of a satisfactory fit and/or dissatisfactory fit may include different gradations, for example a satisfactory fit with minimal leaks, a satisfactory fit with small leaks, a dissatisfactory fit with small leaks, or a dissatisfactory fit with major leaks. Additionally or alternatively, in some embodiments, the processor 302 includes hardware, software, firmware, and/or the like, that causes outputting of warning message(s).

In some embodiments, the apparatus 300 includes input/output circuitry 306 that provides output to the user and, in some embodiments, to receive an indication of a user input. In some embodiments, the input/output circuitry 306 is in communication with the processor 302 to provide such functionality. The input/output circuitry 306 may comprise one or more user interface(s) and in some embodiments includes a display or plurality of displays that comprise(s) the interface(s) rendered as a web user interface, an application user interface, an external user device, a backend system, or the like. In some embodiments, the input/output circuitry 306 also includes a trigger, keyboard, a mouse, a joystick, a touch screen, touch areas, soft keys a microphone, a speaker, or other input/output mechanisms. The processor 302 and/or input/output circuitry 306 comprising the processor may be configured to control one or more functions of one or more user interface elements through computer program instructions (e.g., software and/or firmware) stored on a memory accessible to the processor (e.g., memory 304, and/or the like). In some embodiments, the input/output circuitry 306 includes or utilizes a user-facing application to provide input/output functionality to a client device and/or other display associated with a user. In some embodiments, the input/output circuitry 306 includes a display integrated into the chassis of the apparatus 300.

The communications circuitry 308 includes any means such as a device or circuitry embodied in either hardware or a combination of hardware and software that is configured to receive and/or transmit data from/to a network and/or any other device, circuitry, or module that is part of or in communication with the apparatus 300. In this regard, the communications circuitry 208 includes, for example in some embodiments, a network interface for enabling communications with a wired or wireless communications network. Additionally or alternatively in some embodiments, the communications circuitry 308 includes one or more network interface card(s), antenna(s), bus(es), switch(es), router(s), modem(s), and supporting hardware, firmware, and/or software, or any other device suitable for enabling communications via one or more communications network(s). Additionally or alternatively, the communications circuitry 308 includes circuitry for interacting with the antenna(s) and/or other hardware or software to cause transmission of signals via the antenna(s) or to handle receipt of signals received via the antenna(s). In some embodiments, the communications circuitry 308 enables transmission to and/or receipt of data from a client device in communication with the apparatus 300.

In some embodiments, the apparatus 300 includes captured audio manipulation circuitry 310 includes hardware, software, firmware, and/or a combination thereof, for performing functionality associated with capturing audio data and/or deriving data from captured audio data. For example, in some embodiments the captured audio manipulation circuitry includes internal audio microphone(s), external audio microphone(s), one or more user-audio sensor(s), and/or the like. Alternatively or additionally, in some embodiments, the captured audio manipulation circuitry 310 includes hardware, software, firmware, and/or a combination thereof, that receives internal audio data and/or external audio data, such as by capturing the internal audio data and/or external audio data or receiving the data via transmission from an external device, sensor, and/or the like. Additionally or alternatively, in some embodiments, the captured audio manipulation circuitry 310 includes hardware, software, firmware, and/or a combination thereof, that generates comparative data from the received internal audio data and/or external audio data. For example, the captured audio manipulation circuitry 310 in some embodiments generates comparative internal data based on captured internal audio data, for example by deriving such comparative internal data from the captured internal audio data, applying the captured internal audio data to a filter model, and/or applying the captured internal audio data to an inverse hear-through model. Additionally or alternatively, in some embodiments, the captured audio manipulation circuitry 310 generates comparative external data based on captured external audio data, for example by deriving such comparative external data from the captured external audio data, and/or applying the captured external audio data to a filter model. Additionally or alternatively, in some embodiments, the captured audio manipulation circuitry 310 includes hardware, software, firmware, and/or a combination thereof, that receives user-generated audio. Additionally or alternatively, in some embodiments, the captured audio manipulation circuitry 310 includes hardware, software, firmware, and/or a combination thereof, that stores received and/or derived data. It will be appreciated that, in some embodiments, captured audio manipulation circuitry 310 may include a separate processor, specially configured field programmable gate array (FPGA), or a specially programmed application specific integrated circuit (ASIC).

In some embodiments, the apparatus 300 includes fit determination circuitry 312 includes hardware, software, firmware, and/or a combination thereof, for performing functionality associated with determining whether received data indicates a satisfactory fit. For example, in some embodiments, the fit determination circuitry 312 includes hardware, software, firmware, and/or a combination thereof, that identifies an audio processing mode for use in further processing. In some embodiments, the audio processing mode is identified based on external audio data and/or internal audio data. Additionally or alternatively, in some embodiments, the fit determination circuitry 312 includes hardware, software, firmware, and/or a combination thereof, that retrieves an audio comparison model based on the audio processing mode. Additionally or alternatively, in some embodiments, the fit determination circuitry 312 includes hardware, software, firmware, and/or a combination thereof, that computes energy differential data by applying comparative data and corresponding received data to an audio comparison model. In some embodiments, the energy differential data is computed by applying the comparative internal data and the external audio data to an audio comparison model. Additionally or alternatively, in some embodiments, the fit determination circuitry 312 includes hardware, software, firmware, and/or a combination thereof, that compares energy differential data with at least one threshold to determine whether the energy differential data indicates a satisfactory fit. In some embodiments, the energy differential data indicates a satisfactory fit when the energy differential data satisfies the threshold (e.g., is equal to the threshold in some contexts), and indicates a dissatisfactory fit when the energy differential data does not satisfy the threshold. It will be appreciated that, in some embodiments, fit determination circuitry 312 may include a separate processor, specially configured field programmable gate array (FPGA), or a specially programmed application specific integrated circuit (ASIC).

In some embodiments, the apparatus 300 includes warning generation circuitry 314 includes hardware, software, firmware, and/or a combination thereof, for generating and/or outputting or causing outputting of warning(s) associated with determination(s) of an audio fit, for example whether data indicates a satisfactory fit and/or a dissatisfactory fit. For example, in some embodiments, the warning generation circuitry 314 includes hardware, software, firmware, and/or a combination thereof, that identifies a determination of whether received data indicates a satisfactory fit, for example by determining whether the energy differential data satisfied or did not satisfy at least one warning threshold. Additionally or alternatively, in some embodiments, the warning generation circuitry 314 includes hardware, software, firmware, and/or a combination thereof, that causes outputting of a warning message via at least one output component associated with an audio protector. In some embodiments, the warning message includes renderable data, an audio message for output via a client device, audio message for output via a warning speaker, and/or data for activating a warning visual indicator of a warning system (e.g., a warning light or alarm system). Additionally or alternatively, in some embodiments, the warning generation circuitry 314 includes hardware, software, firmware, and/or a combination thereof, that activates one or more output component(s) based at least in part on a determination of a dissatisfactory fit (e.g., based on comparison of energy differential data to at least one warning threshold). Additionally or alternatively, in some embodiments, the warning generation circuitry 314 includes hardware, software, firmware, and/or a combination thereof, that outputs warning message(s) via the apparatus 300. It will be appreciated that, in some embodiments, warning generation circuitry 314 may include a separate processor, specially configured field programmable gate array (FPGA), or a specially programmed application specific integrated circuit (ASIC).

In some embodiments, one or more of the sets of circuitries 302-314 are combinable. Alternatively or additionally, in some embodiments, one or more of the sets of circuitry perform some or all of the functionality described associated with another component. For example, in some embodiments, one or more of the sets of circuitry 302-314 are combined into a single module embodied in hardware, software, firmware, and/or a combination thereof. Similarly, in some embodiments, one or more of the sets of circuitry, for example, captured audio manipulation circuitry 310, fit determination circuitry 312, and/or warning generation circuitry 314, is/are combined such that the processor 302 performs one or more of the operations described above with respect to each of these sets of circuitry.

Example Data Flows and Data Architectures of the Disclosure

Having described example systems and apparatuses in accordance with embodiments of the present disclosure, example data architectures and data flows for processing data in accordance with the present disclosure will now be discussed. In some embodiments, the systems and/or apparatuses described herein maintain data environment(s) that enable the data flows described herein. For example, in some embodiments, the systems and/or apparatuses described herein function in accordance with the data flow depicted in FIGS. 4 and 5, and the data architectures depicted and/or described with respect to FIG. 6. For purposes of brevity and clarity, the data flows and data architectures are depicted and described with respect to an apparatus 300, for example embodying a specially configured audio protector 200.

Figure 4:
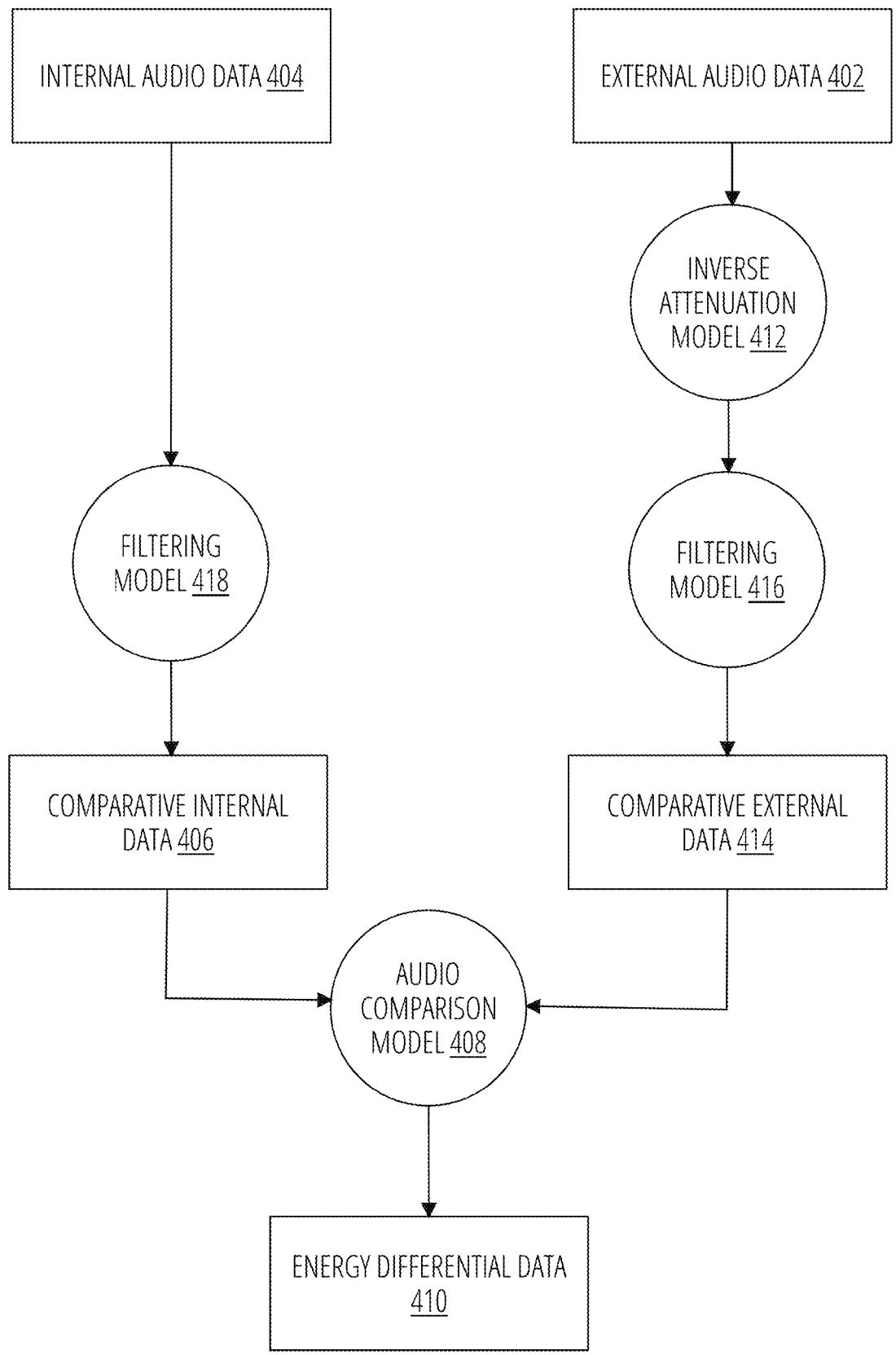
FIG. 4 illustrates an example data flow for fit testing in accordance with at least one embodiment of the present disclosure.

FIG. 4 illustrates an example data flow for fit testing in accordance with at least one embodiment of the present disclosure. In some embodiments, a specially configured apparatus—such as the apparatus 300—maintains one or more computing environment(s), for example embodied in hardware, software, firmware, and/or a combination thereof, that enables the data flow. In some embodiments, the apparatus 300 executes one or more software application(s) that maintains the computing environment(s) for performing the data flow(s).

As illustrated in FIG. 4, the apparatus 300 maintains internal audio data 404 and external audio data 402. The external audio data 402 may represent audio signals captured from an environment of an audio protector before attenuation by one or more component(s) of the audio protector. The internal audio data 404 may represent audio signals captured from an internal portion of an audio protector after attenuation by one or more component(s) of the audio protector, for example by one or more dampener(s) of the audio protector that surround a user's ear during use and/or that is inserted within the user's ear during use. In this regard, the internal audio data 404 may correspond to audio signals at risk of impacting the wearer's hearing. In some embodiments, the internal audio data 404 and/or the external audio data 402 is retrieved from one or more datastore(s) to which they were previously stored. In some embodiments, the internal audio data 404 is captured and/or received from one or more internal protector microphone(s) of or communicable with the apparatus 300. Additionally or alternatively, in some embodiments, the external audio data 402 is captured and/or received from one or more external protector microphone(s) of or communicable with the apparatus 300.

In some embodiments, the internal audio data 404 is manipulated and/or otherwise processed for use in further processing. As depicted for example, in some embodiments, the internal audio data 404 is applied to a filtering model 418. The filtering model 418 in some embodiments segments the internal audio data 404 into particular defined frequency bands. In this regard, the filtering model 418 may generate comparative internal data 406 representing the energy levels and/or other data values associated with each frequency band of the internal audio data 404. In some embodiments, the filtering model 418 includes one or more audio filter(s) that segment a particular frequency and/or plurality of frequencies, and/or that approximates attenuation of audio signal(s) by one or more dampener(s) or other component(s) of an audio protector. Alternatively or additionally, in some embodiments, the filtering model is embodied by an algorithmic model, specially trained learning model, or the like, that represents filtering, passing, attenuation, and/or the like of a particular frequency band.

In some embodiments, the external audio data 402 is applied to an inverse attenuation model 412. The inverse attenuation model 412 embodies one or more statistical, algorithmic, and/or machine learning model(s) that approximate attenuation of the external audio data 402 by component(s) of a particular audio protector. The inverse attenuation model 412 specifically may represent attenuation by such component(s) in a circumstance where the audio protector is worn with a particular desired fit (e.g., a good fit, a satisfactory fit, or otherwise a best fit). In this regard, the inverse attenuation model 412 may generate estimated internal audio data that represents data values after expected attenuation of signals represented by particular, for example the external audio data 402, by that audio protector. Non-limiting examples of data representing and/or for configuring an inverse attenuation model 412 are described herein with respect to FIGS. 11 and 12.

In some embodiments, the data generated by the inverse attenuation model 412 (for example, estimated internal audio data) is similarly applied to a filtering model 416. In some embodiments, the filtering model 416 segments the data generated from the inverse attenuation model 412 into particular defined frequency bands. Such frequency bands may correspond to the same frequency bands represented in the comparative internal data 406. In this regard, the filtering model 416 may generate comparative external data 414 representing the energy levels and/or other data values associated with each frequency band of the estimated internal audio data generated via the inverse attenuation model 412. The resulting comparative external data 414 may represent an estimation or prediction of the attenuation of the external audio data 402 at different frequency bands that is achieved by a particular audio protector when worn in a particular fit. In this regard the comparative external data 414 represents the expected values at each frequency band that is expected to be represented in the comparative internal data in a circumstance where the audio protector is worn with a particular fit (e.g., a satisfactory or good fit).

In some embodiments, the apparatus 300 derives the comparative internal data 406 and the comparative external data 414 for further comparison. As depicted, the apparatus 300 applies the comparative internal audio data 406 together with the comparative external data 414 to an audio comparison model 408. The audio comparison model 408 then generates energy differential data 410 from at least such inputs. In some embodiments, the audio comparison model 408 embodies a statistical, algorithmic, and/or machine-learning model specifically trained to identify differences between the comparative internal data 406 and the comparative external data 414 via comparison. In some embodiments, the energy differential data 410 represents a difference in energy and/or other characteristics between the comparative internal data 406 and/or the comparative external data 414. In some embodiments, such differences are indicated for each particular frequency band, for example such that identification of particular frequency band differences is determinable via the energy differential data 410. In some embodiments, the apparatus 300 identifies a particular audio comparison model 408 for use. In some such embodiments, the apparatus 300 identifies the particular audio comparison model 408 based at least in part on a corresponding audio processing mode identified by the apparatus 300, for example as depicted and described with respect to FIG. 6 herein. In some embodiments, the apparatus 300 identifies a particular audio comparison model 410 for use. In some such embodiments, the apparatus 300 may identify the audio processing mode and corresponding audio comparison model 410 as depicted and described with respect to FIG. 6 herein.

The energy differential data 410 is usable to determine whether the received and/or captured data indicates a satisfactory fit of an audio protector. For example, the energy differential data 410 in some embodiments is comparable to one or more threshold(s) that delineate between a satisfactory fit and a dissatisfactory fit. In some embodiments, the energy differential data 410 is comparable to one or more threshold(s) embodying a threshold value to determine whether the energy differential data 410 is equivalent to the threshold value. In other embodiments, the energy differential data 410 is comparable to one or more threshold(s) embodying a range of values indicating a satisfactory fit to determine whether the energy differential data 410 falls within the range of values. In this regard, the determination of whether the data indicates a satisfactory fit (e.g., based at least in part on the comparison) is utilized for outputting any of a number of warning message(s), for example indicating whether a fit is satisfactory or dissatisfactory, indicating a warning of possible hearing harm due to dissatisfactory fit of an audio protector, and/or the like.

Figure 5:
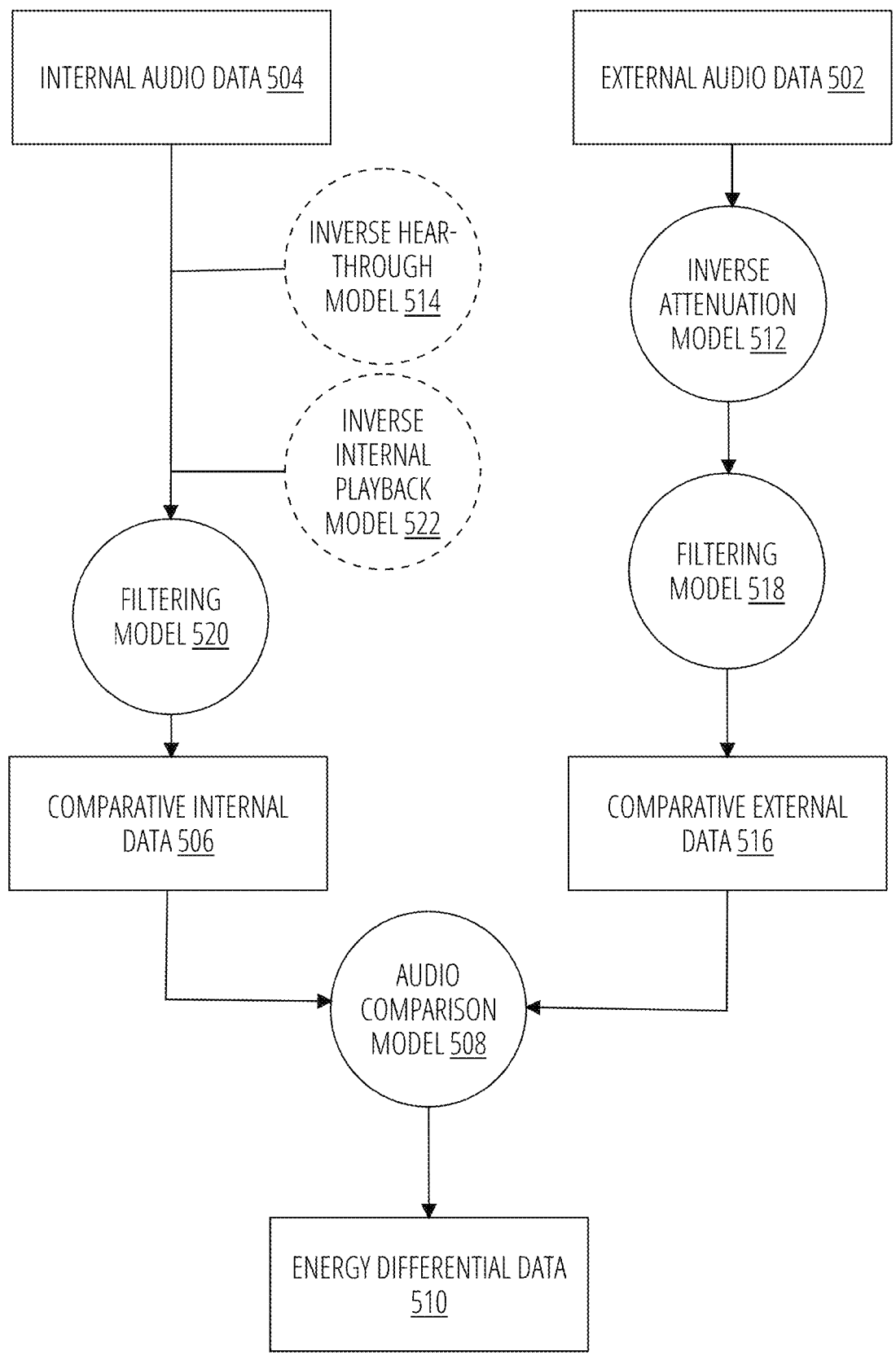
FIG. 5 illustrates another example data flow for fit testing an audio protector with additional internal audio effects pre-processing in accordance with at least one embodiment of the present disclosure.

FIG. 5 illustrates another example data flow for fit testing an audio protector having additional internal audio effects pre-processing in accordance with at least one embodiment of the present disclosure. Specifically, FIG. 5 depicts an example data flow for fit testing an audio protector with optional hear-through capabilities and/or internal audio playback capabilities in accordance with at least one embodiment of the present disclosure. In some embodiments, a specially configured apparatus—such as the apparatus 300 configured with hear-through capabilities and/or internal audio playback capabilities—maintains one or more computing environment(s), for example embodied in hardware, software, firmware, and/or a combination thereof, that enables the data flow. In some embodiments, the apparatus 300 executes one or more software application(s) that maintains the computing environment(s) for performing the data flow(s).

As illustrated in FIG. 5, the apparatus 300 maintains internal audio data 504 and external audio data 502. In some embodiments, the apparatus 300 maintains internal audio data 504 and external audio data 502. The external audio data 502 may represent audio signals captured from an environment of an audio protector before attenuation by one or more component(s) of the audio protector. The internal audio data 504 may represent audio signals captured from an internal portion of an audio protector after attenuation by one or more component(s) of the audio protector, for example by one or more dampener(s) of the audio protector that surround a user's ear during use and/or that is inserted within the user's ear during use. In this regard, the internal audio data 504 may correspond to audio signals at risk of impacting the wearer's hearing. In some embodiments, the internal audio data 504 and/or the external audio data 502 is retrieved from one or more datastore(s) to which they were previously stored. In some embodiments, the internal audio data 504 is captured and/or received from one or more internal protector microphone(s) of or communicable with the apparatus 300. Additionally or alternatively, in some embodiments, the external audio data 502 is captured and/or received from one or more external protector microphone(s) of or communicable with the apparatus 300.

In some embodiments, the internal audio data 504 is manipulated and/or otherwise processed for use in further processing. For example, in some embodiments, the internal audio data 504 is processed to diminish or eliminate the effects of hear-through capabilities on audio fit testing. In some embodiments, as depicted, the internal audio data 504 is applied to an inverse hear-through model 514. Hear-through may enable certain audio signals (e.g., audio signals within a particular frequency band, and/or audio signal(s) at a particular energy level) to be played through an output component on the internal potion of the audio protector, such that these audio signals may be heard by the wearer even in a circumstance where other audio signals are attenuated by the audio protector. It should be appreciated, however, that such hear-through capabilities may allow the ambient sounds to be heard more easily within the internal portion of the audio protector, but may also affect the audio fit testing process(es) described herein. In some embodiments, the inverse hear-through model 514 embodies an algorithmic, machine-learning, and/or statistical model that compensates of the presence of hear-through data produced on the internal portion of the audio protector and that may be captured by one or more internal protector microphone(s). In some embodiments, the inverse hear-through model 514 is configured based at least in part on the transfer function between the audio output component (e.g., a speaker) utilized for hear-through and the internal protector microphone(s). Alternatively or additionally, in some embodiments, the inverse hear-through model 514 is derived based at least in part on the inverse of the frequency response and phase response defining a particular transfer function, for example to compensate or eliminate the transfer function.

In some embodiments, the inverse hear-through model 514 is tuned to compensate for one or more additional parameters. For example, in some embodiments, the inverse hear-through model 514 is tuned to compensate for volume at which the signals passed through via hear-through are produced by the audio output component associated with the hear-through signals. In this regard, the inverse hear-through model 514 may be dynamically updatable based on current hear-through settings to compensate for the current settings of hear-through capabilities, for example based on the current volume settings, such that the inverse hear-through model 514 may be updated automatically by the apparatus 300 or automatically by itself accordingly to compensate for the current settings. It will be appreciated that in circumstances where an audio protector is not equipped with hear-through capabilities, such an inverse hear-through model 514 may be optional and/or omitted entirely.

It should be appreciated that in some embodiments, hear-through capabilities and audio fit testing capabilities may be associated with different external protector microphones. For example, the apparatus 300 may include at least one first external protector microphone that captures external audio data utilized for audio fit testing, and at least one second external protector microphone utilized for hear-through processing. Alternatively or additionally, in some embodiments, the apparatus 300 shares the same external protector microphone(s) for both capabilities. In this regard, in some embodiments the apparatus 300 may split external audio data into two separate portions utilized for each of the capabilities. For example, the apparatus 300 may split signals captured by the external protector microphone(s) into a first external audio data utilized by a hear-through circuit that performs the hear-through process(es), and second external audio data that performs the automatic audio fit testing process(es) described herein.

In some embodiments, the inverse hear-through model 514 generates processed internal audio data. The processed internal audio data may represent the internal audio data 504 with effects from hear-through capabilities of the audio protector removed.

In some embodiments, the processed internal audio data generated via the inverse hear-through model 514 is applied to a filtering model 520. The filtering model 520 in some embodiments segments the processed internal audio data into particular defined frequency bands. In this regard, the filtering model 520 may generate comparative internal data 506 representing the energy levels and/or other data values associated with each frequency band of the processed internal audio data. In some embodiments, the filtering model 520 includes one or more audio filter(s) that segment a particular frequency and/or plurality of frequencies, and/or that approximates attenuation of audio signal(s) by one or more dampener(s) or other component(s) of an audio protector. Alternatively or additionally, in some embodiments, the filtering model is embodied by an algorithmic model, specially trained learning model, or the like, that represents filtering, passing, attenuation, and/or the like of a particular frequency band.

Alternatively or additionally, in some embodiments, the internal audio data 504 is applied to an inverse internal playback model 522. For example, in some embodiments, the internal audio data 504 is processed to diminish or eliminate the effects of sourced audio (e.g., music, a phone call, and/or the like) being played back by internal speaker(s) and/or other output source(s) within the internal portion of an audio protector. In one example context, a wearer may utilize such playback capabilities to play music via a wired or wireless connection between the audio protector and an external device (e.g., the user's phone), for example via an AUX connection, Bluetooth connection, and/or Wi-Fi connection between such devices. In circumstances where internal playback of such audio reaches a certain level, audio signals produced for such internal playback may be captured by internal protector microphone(s) and affect the corresponding internal audio data 504. In circumstances where an audio protector is properly fit on its wearer, the effects of such internal playback may increase as signals are "trapped" within the internal portion of the audio protector, and thereby are more likely to affect the automatic fit testing process(es) described herein.

The inverse internal playback model 522 generates processed internal audio data that removes the effects of internal playback audio from the internal audio data 504. In some embodiments, the inverse internal playback model 522 includes a compensation algorithm based on the transfer function between an inner speaker that outputs the internal playback audio and the internal protector microphone(s) that capture the internal audio data 504. In this regard, based on the module frequency response and/or phase frequency response, the inverse internal playback model 522 may be configured to inverse the effects of such internal playback audio on the internal protector microphone(s).

Additionally or alternatively, in some embodiments, the inverse internal playback model 522 is configured based at least in part on one or more current playback setting value(s). In some embodiments, the inverse internal playback model 522 is configured based at least in part on volume settings for the internal playback. Additionally or alternatively, the inverse internal playback model 522 is configured to operate when internal playback is active, such that the inverse internal playback model 522 is not utilized unless internal playback is currently activated. In this regard, in some such embodiments the inverse internal playback model 522 is configured to mitigate or remove the effects of such internal playback audio on internal audio data 504.

In some embodiments, the automatic fit testing process(es) described herein are not initiate in circumstances where internal audio playback is active. Alternatively or additionally, in some embodiments a notice is outputted to the wearer—visually via an indicator, visually via a user interface, auditorily via an audio output component (e.g., a speaker) in the internal portion of the audio protector)—indicating that internal audio playback must be stopped to perform the automatic fit testing process(es) described herein.

In some embodiments, a plurality of models may be utilized to remove various effects from the internal audio data 504. For example, in some embodiments, internal audio data 504 is applied to the inverse hear-through model 514, and the processed audio data generated from the inverse hear-through model 514 is subsequently applied to the inverse internal playback model 522. The inverse-hear through model 514 may generate subsequently processed data that is then applied to the filtering model 520, for example. Alternatively, in some embodiments internal audio data 504 is applied to the inverse internal playback model 522, and the output from the inverse internal playback model 522 is subsequently applied to the inverse hear-through model 514. The subsequently processed internal audio data output from the inverse hear-through model 514 may then be applied to the filtering model 520.

Alternatively or additionally, an audio protector may be configured with only one of the inverse models for compensating internal audio data 504. For example, some embodiments are configured to utilize only the inverse hear-through model 514, or only the inverse internal playback model 522. Some such embodiments are configured with the model(s) that are specific to the capabilities of an audio protector, for example where an audio protector that offers playback capabilities but not hear-through capabilities is configured to utilize the inverse internal playback model 522 only and/or an audio protector that offers hear-through capabilities but not playback capabilities is configured to utilize the inverse hear-through model 514 only. Alternatively or additionally still, some embodiments utilize neither such models, such that internal audio data 504 is processed as part of automatic fit testing process(es) without pre-processing via either such model(s).

In some embodiments, the external audio data 502 is applied to an inverse attenuation model 512. The inverse attenuation model 512 embodies one or more statistical, algorithmic, and/or machine learning model(s) that approximate attenuation of the external audio data 502 by component(s) of a particular audio protector. The inverse attenuation model 512 specifically may represent attenuation by such component(s) in a circumstance where the audio protector is worn with a particular desired fit (e.g., a good fit, a satisfactory fit, or otherwise a best fit). In this regard, the inverse attenuation model 512 may generate estimated internal audio data that represents data values after expected attenuation of signals represented by particular, for example the external audio data 502, by that audio protector. Non-limiting examples of data representing and/or for configuring an inverse attenuation model 512 are described herein with respect to FIGS. 11 and 12.

In some embodiments, the data generated by the inverse attenuation model 512 (for example, estimated internal audio data) is similarly applied to a filtering model 518. In some embodiments, the filtering model 518 segments the data generated from the inverse attenuation model 512 into particular defined frequency bands. Such frequency bands may correspond to the same frequency bands represented in the comparative internal data 506. In this regard, the filtering model 518 may generate comparative external data 516 representing the energy levels and/or other data values associated with each frequency band of the estimated internal audio data generated via the inverse attenuation model 512. The resulting comparative external data 516 may represent an estimation or prediction of the attenuation of the external audio data 502 at different frequency bands that is achieved by a particular audio protector when worn in a particular fit. In this regard the comparative external data 516 represents the expected values at each frequency band that is expected to be represented in the comparative internal data 506 in a circumstance where the audio protector is worn with a particular fit (e.g., a satisfactory or good fit).

In some embodiments, the apparatus 300 processes the comparative internal data 506 and the comparative external data 516 for further comparison. As depicted, the apparatus 300 applies the comparative internal audio data 506 together with the comparative external data 516 to an audio comparison model 508. The audio comparison model 508 then generates energy differential data 510 from at least such inputs. In some embodiments, the audio comparison model 508 embodies a statistical, algorithmic, and/or machine-learning model specifically trained to identify differences between the comparative internal data 506 and the comparative external data 516 via comparison. In some embodiments, the energy differential data 510 represents a difference in energy and/or other characteristics between the comparative internal data 506 and/or the comparative external data 516. In some embodiments, such differences are indicated for each particular frequency band, for example such that identification of particular frequency band differences is determinable via the energy differential data 510. In some embodiments, the apparatus 300 identifies a particular audio comparison model 508 for use. In some such embodiments, the apparatus 300 identifies the particular audio comparison model 508 based at least in part on a corresponding audio processing mode identified by the apparatus 300, for example as depicted and described with respect to FIG. 6 herein. In some embodiments, the apparatus 300 identifies a particular audio comparison model 510 for use. In some such embodiments, the apparatus 300 may identify the audio processing mode and corresponding audio comparison model 510 as depicted and described with respect to FIG. 6 herein.

The energy differential data 510 is usable to determine whether the received and/or captured data indicates a satisfactory fit of an audio protector. For example, the energy differential data 510 in some embodiments is comparable to one or more threshold(s) that delineate between a satisfactory fit and a dissatisfactory fit. In some embodiments, the energy differential data 510 is comparable to one or more threshold(s) embodying a threshold value to determine whether the energy differential data 510 is equivalent to the threshold value. In other embodiments, the energy differential data 510 is comparable to one or more threshold(s) embodying a range of values indicating a satisfactory fit to determine whether the energy differential data 510 falls within the range of values. In this regard, the determination of whether the data indicates a satisfactory fit (e.g., based at least in part on the comparison) is utilized for outputting any of a number of warning message(s), for example indicating whether a fit is satisfactory or dissatisfactory, indicating a warning of possible hearing harm due to dissatisfactory fit of an audio protector, and/or the like.

Figure 6:
FIG. 6 illustrates an example architecture of a data table in accordance with at least one embodiment of the present disclosure.

FIG. 6 illustrates an example architecture of a data table in accordance with at least one embodiment of the present disclosure. Specifically, FIG. 6 depicts a mode table 602 that may be maintained for performing the automatic fit testing processes described herein. In some embodiments, the mode table 602 is generated and/or otherwise maintained by the apparatus 300. The mode table 602 may be utilized by the apparatus 300 in some embodiments to determine a particular audio processing mode in which to operate the apparatus 300 for further processing as part of the automatic fit testing processes in accordance with the present disclosure.

As illustrated, the mode table 602 indicates a plurality of different modes and associated data values for particular data properties associated with each mode. Specifically, the mode table 602 includes an indication of a particular mode associated with corresponding determinations for an audio energy level corresponding external audio data and an indication of whether user-generated audio is detected. In this regard, the apparatus 300 may receive data, derive value(s) for such data properties based on the received data, and identify an audio processing mode from the derived data value(s) corresponding to such data properties. In the example context as depicted, the apparatus 300 may derive a first value indicating whether user-generated audio is detected in received data, and the apparatus 300 may derive a second value indicating whether an audio energy level for the received data is below, between, or above one or more particular threshold(s), and utilize the first value and the second value to determine a corresponding audio processing mode utilizing the mode table 602.

In some embodiments, the apparatus 300 determines a first value indicating whether user-generated audio is detected within received internal and/or external audio data. For example, in some embodiments, the apparatus 300 processes the external audio data using a specially configured user-generated audio detection algorithm. The user-generated audio detection algorithm may parse the external audio data to detect particular indicator(s) of user speech, particular tones or user-generated sounds, particular trigger words, phrases, and/or the like, or other particular detectable audio. In some embodiments, the user-generated audio is captured via a separate user-audio sensor, such that user-generated audio is detected in a circumstance where the user-audio sensor receives user-generated audio and/or detects the particular data from captured audio signal(s). In some embodiments, a user-audio sensor is specially configured to detect particular frequency range(s), particular data indicator(s) in captured audio data, and/or the above data-driven determination(s). The user-audio sensor may include or be embodied by an integrated microphone, a boom microphone, an external microphone attached to the apparatus 300, and/or the like.

In some embodiments, the apparatus 300 determines a second value indicating a particular range within which an energy level for particular audio data falls. In some embodiments, the apparatus 300 determines data representing an energy level associated with external audio data captured associated with a particular audio protector. In this regard, the energy level may correspond to, and be based upon, how loud the environment surrounding the audio protector is at a particular time. As depicted, "E" referred to in the mode table 602 embodies the data representing the energy level associated with the external audio data.

In some embodiments, the apparatus 300 determines the second value indicating the particular range within which the energy level falls based at least in part on one or more threshold(s). For example, in some embodiments, the apparatus 300 determines whether the second value falls within a first range below a minimum threshold (E<MINIMUM THRESHOLD), a second range between a minimum threshold and a maximum threshold (MAXIMUM THRESHOLD>E>MINIMUM THRESHOLD), or a third range above a maximum threshold (E>MAXIMUM THRESHOLD). The apparatus 200 may compare the data representing the energy level with the minimum threshold and/or maximum threshold to determine whether the energy level falls within the first range, the second range, or the third range. In this regard, the apparatus 300 may determine the second value indicating the results of such comparison(s) (e.g., indicating whether the energy level fell within the first range, the second range, or the third range).

In some embodiments, the apparatus 300 utilizes the first value indicating whether user-generated audio is detected within received internal and/or external audio data and the second value indicating the particular range within which the energy level falls to identify a corresponding audio mode. In some embodiments, the apparatus 300 utilizes the first value and the second value as a key for retrieving a corresponding audio processing mode via the mode table 602. In this regard, the mode table 602 may be utilized to assign different modes to different combinations of the first value indicating whether user-generated audio is detected within received audio data and the second value indicating the particular range within which the energy level falls. In some embodiments, each combination of the first value and the second value is associated with a different audio processing mode. In some embodiments, two or more combinations of the first value and the second value are associated with the same mode. For example, in some embodiments, the apparatus 300 determines an audio processing mode using the mode table 602 for further use. In some embodiments, the apparatus 300 utilizes the determined audio processing mode to identify and/or retrieve a particular model corresponding to the audio processing mode, for example a particular audio comparison model.

As illustrated, the mode table 602 maintains associations between particular values for the first value and particular values for the second value with particular audio processing modes. For example, the mode table 602 includes a first association between a first value indicating user-generated audio is detected (e.g., USER-GENERATED AUDIO DETECTED=YES) and a second value indicating the energy level of particular received audio data is above a maximum threshold (e.g., E>MAXIMUM THRESHOLD) with a first audio processing mode (e.g., MODE=MODE 1). The mode table 602 further includes a second association between a first value indicating user-generated audio is not detected (e.g., USER-GENERATED AUDIO DETECTED=NO) and a second value indicating the energy level of particular received audio data is above a maximum threshold (e.g., E>MAXIMUM THRESHOLD) similarly with the first audio processing mode (e.g., MODE=MODE 1). In some embodiments, a second value representing that E>MAXIMUM THRESHOLD indicates an environment at a significantly loud level. In this regard, it will be appreciated that the apparatus 300 is configured such that regardless of whether user-generated audio data is detected, a corresponding first audio processing mode is usable to process audio data in a circumstance where the energy level indicates a significantly loud level in the environment associated with the audio protector.

Further as illustrated, the mode table 602 includes a third association between a first value indicating user-generated audio is detected (e.g., USER-GENERATED AUDIO DETECTED=YES) and a second value indicating the energy level of particular received audio data falls between a maximum threshold and a minimum threshold (e.g., MAXIMUM THRESHOLD>E>MINIMM THRESHOLD) with a second audio processing mode (e.g., MODE=MODE 2). The mode table 602 further includes a fourth association between a first value indicating user-generated audio is not detected (e.g., USER-GENERATED AUDIO DETECTED=NO) and a second value indicating the energy level of particular received audio data is between a maximum threshold and a minimum threshold (e.g., MAXIMUM THRESHOLD>E>MINIMUM THRESHOLD) with a third audio processing mode (e.g., MODE=MODE 3). In some embodiments, a second value representing that MAXIMUM THRESHOLD>E>MINIMUM THRESHOLD indicates an environment at a moderately loud level. In this regard, the apparatus 300 may utilize a different audio processing mode to process audio data of a moderately loud level based on whether user-generated audio is detected. In some embodiments, the different modes correspond to different models (e.g., different audio comparison models) that are specially configured to process audio data in circumstances where user-generated audio is present or not present.

Further as illustrated, the mode table 602 includes a fifth association between a first value indicating user-generated audio is detected (e.g., USER-GENERATED AUDIO DETECTED=YES) and a second value indicating the energy level of particular received audio data falls below a minimum threshold (e.g., E<MINIMUM THRESHOLD) with a fourth audio processing mode (e.g., MODE=MODE 4). The mode table 602 further includes a sixth association between a first value indicating user-generated audio is not detected (e.g., USER-GENERATED AUDIO DETECTED=NO) and a second value indicating the energy level of particular received audio data falls below a minimum threshold (e.g., E<MINIMUM THRESHOLD) with a fifth audio processing mode (e.g., MODE=MODE 5). In some embodiments, a second value representing that E<MINIMUM THRESHOLD indicates an environment at a quiet level. In this regard, the apparatus 300 may utilize a different audio processing mode to process audio data of a quiet level based on whether user-generated audio is detected. In some embodiments, mode 5 is associated with output indicating that the audio testing process cannot be meaningfully performed, such that a fit result is not available. However, this result may be acceptable as the quiet level of ambient noise means the user is not at risk of hearing damage. In some embodiments, the different modes correspond to different models (e.g., different audio comparison models) that are specially configured to process audio data in circumstances where user-generated audio is present or not present.

In some embodiments, the different audio processing modes are each associated with different model(s) specially configured to process data particular to that mode. For example, the fourth audio processing mode may correspond to particular model(s) that are specially configured to handle circumstances where sufficient energy level ambient data is not detected, but user-generated audio is detected. This mode may correspond to a particular process that utilizes a particular audio comparison model, for example, that performs accurately when only user-generated audio data is detected. Comparatively, a second mode such as the first audio processing mode may correspond to particular model(s) that are specially configured to handle circumstances where sufficient energy level ambient data is detected that drowns out any user-generated audio. Such a mode may correspond to another process that utilizes a different particular audio comparison model, for example, that performs accurately in very loud environments (e.g., utilizing training data from such environments).

It will be appreciated that in some embodiments, the detection of user-generated audio is optional. In some embodiments, the apparatus 300 determines a mode based only on energy level(s) determined for external audio data and/or internal audio data. Alternatively or additionally, in some embodiments, the apparatus 300 determines a mode based at least in part on one or more other data-driven determination(s).

Example Processes of the Disclosure

Having described example systems and apparatuses, data architectures, and data flows in accordance with embodiments of the present disclosure, example processes of the disclosure will now be discussed. It will be appreciated that each of the flowcharts depicts an example computer-implemented process that is performable by one or more of the apparatuses, systems, devices, and/or computer program products described herein, for example utilizing one or more of the specially configured components thereof.

The blocks indicate operations of each process. Such operations may be performed in any of a number of ways, including, without limitation, in the order and manner as depicted and described herein. In some embodiments, one or more blocks of any of the processes described herein occur in-between one or more blocks of another process, before one or more blocks of another process, in parallel with one or more blocks of another process, and/or as a sub-process of a second process. Additionally or alternatively, any of the processes in various embodiments include some or all operational steps described and/or depicted, including one or more optional blocks in some embodiments. With regard to the flowcharts illustrated herein, one or more of the depicted block(s) in some embodiments is/are optional in some, or all, embodiments of the disclosure. Optional blocks are depicted with broken (or "dashed") lines. Similarly, it should be appreciated that one or more of the operations of each flowchart may be combinable, replaceable, and/or otherwise altered as described herein.

Figure 7:
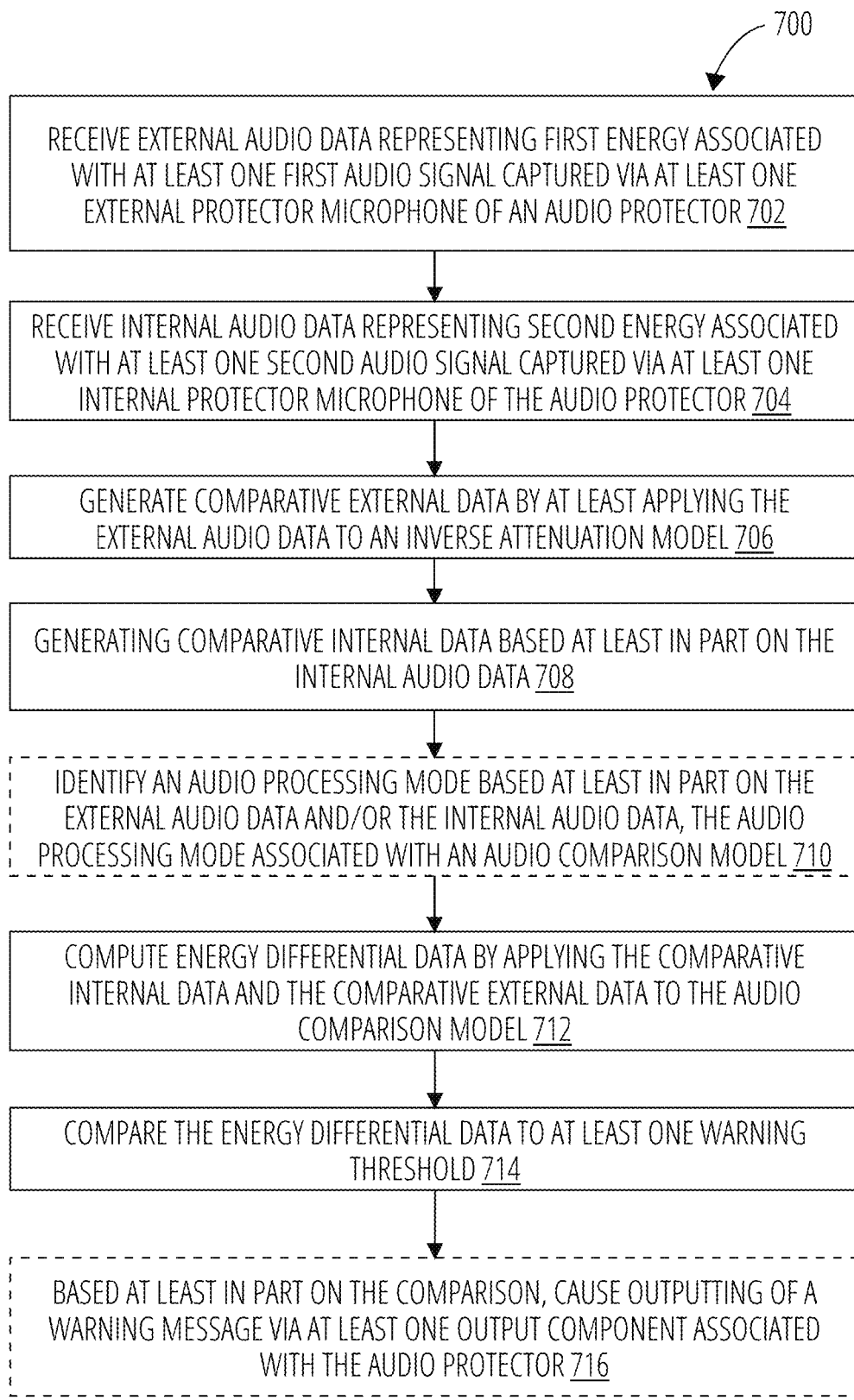
FIG. 7 illustrates a flowchart depicting operations of an example process for performing a fit test in accordance with at least one embodiment of the present disclosure.

FIG. 7 illustrates a flowchart depicting operations of an example process for performing a fit test in accordance with at least one embodiment of the present disclosure. Specifically, FIG. 7 depicts operations of an example process 700. In some embodiments, the process 700 is embodied by computer program code stored on a non-transitory computer-readable storage medium of a computer program product configured for execution to perform the process as depicted and described. Alternatively or additionally, in some embodiments, the process 700 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one user device, warning system, external output component, and/or the like. For purposes of simplifying the description, the process 700 is described as performed by and from the perspective of the apparatus 300.

The process 700 begins at operation 702. At operation 702, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that receives external audio data. In some embodiments, the external audio data represents characteristic(s)—including at least a first energy for example—for at least one first audio signal captured via at least one external protector microphone of an audio protector. Additionally or alternatively, in some embodiments, the external audio data includes data associated with a plurality of frequency ranges. For example, in some embodiments, the audio protector includes one or more external protector microphones that capture data from the environment of the audio protector before attenuation by any sound dampener(s) or other components that attenuate sound before it reaches the ears of a wearer of the audio protector. The external protector microphone may be on or a subcomponent of the audio protector itself, or in some embodiments separate from the audio protector.

At operation 704, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that receives internal audio data. In some embodiments, the internal audio data represents characteristic(s)—including at least a second energy for example—for at least one second audio signal captured via at least one internal protector microphone of an audio protector. Additionally or alternatively, in some embodiments, the internal audio data includes data associated with a plurality of frequency ranges. Such frequency ranges may in some embodiments correspond to the same frequency ranges as those represented by corresponding external audio data. For example, in some embodiments, the audio protector includes one or more external protector microphones that capture data from within an internal portion of the audio protector. The internal portion of the audio protector in some embodiments is a portion of the audio protector enclosed by at least one sound dampener, and where the sound impacts the user's ears.

At operation 706, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that generates comparative external data. In some embodiments, the apparatus 300 generates the comparative external data by at least applying the external audio data to an inverse attenuation model. In some embodiments, the inverse attenuation model represents attenuation by a particular audio protector for a particular fit. In this regard, data applied to the inverse attenuation model may be processed in a manner that estimates the expected effects of attenuation by the particular audio protector when worn with the particular fit corresponding to the inverse attenuation model. The inverse attenuation model in some embodiments includes an algorithmic, machine-learning, and/or statistical model that embodies or represents one or more equalization filters.

Additionally or alternatively, in some embodiments, the comparative external data is represents particular filtered frequency ranges. In some embodiments, the comparative external data represents particular filtered frequency ranges filtered from the data generated via the inverse attenuation model. In this regard, the comparative external data may represent particular data characteristics represented in the data generated via the inverse attenuation model of each frequency band of a particular plurality of frequency bands, for example energy levels at each frequency band. In some embodiments, the apparatus 300 generates comparative external data via at least one filtering model, for example by applying the estimated internal audio data generated by the inverse attenuation model to at least one filtering model embodying or comprising at least one audio filter.

At operation 708, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that generates comparative internal data based at least in part on the internal audio data. In some embodiments, the comparative internal data represents particular filtered frequency ranges of the internal audio data. In this regard, the comparative internal data may represent particular data characteristics represented in the internal audio data of each frequency band of a particular plurality of frequency bands, for example energy levels at each frequency band. In some embodiments, the apparatus 300 generates comparative internal data via at least one filtering model, for example by applying the internal audio data to at least one filtering model embodying or comprising at least one audio filter. It should be appreciated that in some embodiments the same at least one filtering model applied to the internal audio data and the data generated via the inverse attenuation model, resulting in the same frequency bands for each of such data represented in the comparative internal data and the comparative external data.

At operation 710, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that identifies an audio processing mode based at least in part on the external audio data and/or the internal audio data. For example, in some embodiments, an energy level is determined based at least in part on an energy level of the external audio data, and the audio processing mode is identified based at least in part on the energy level. Additionally or alternatively, in some embodiments, the apparatus 300 determines whether user-generated audio is detected within the external audio data and/or the internal audio data, and the audio processing mode is identified based at least in part on the determination of whether user-generated audio is detected in the external audio data and/or internal audio data. In some embodiments, the audio processing mode is associated with a particular audio comparison model. In some such embodiments, the apparatus 300 identifies a particular audio processing mode based at least in part on the internal audio data and/or external audio data, and subsequently identifies the audio comparison model corresponding to the identified audio processing mode. In some embodiments, the apparatus 300 is configured to determine between an energy-level based mode and a speech-detection based mode.

In some embodiments, the identified mode corresponds to a particular audio comparison model that processes particular portions of the internal comparison data and/or the external comparison data. For example, in some embodiments, in circumstances where the apparatus 300 detects user-generated audio, a particular mode may be activated that corresponds to an audio comparison model that processes a particular low-pass frequency range (e.g., under 100 Hz). Such a comparison model may be utilized in circumstances where user-generated audio is detected and not drowned out by excessive ambient noise. The low-pass frequency range may correspond to any frequency range within which changes to the data is determined to be most noticeable and/or trackable. Alternatively or additionally, in some embodiments, in circumstances where no user-generated audio is detected, a particular mode may be activated that corresponds to an audio comparison model that processes one or more separate frequency bands, for example a low-pass frequency range at and under 1000 Hz and a high-pass frequency range above 1000 Hz. It will be appreciated that the boundary condition(s) for frequency band(s) may be determined from testing to determine applicable cutoff points, and/or set by a user, or otherwise predetermined based at least in part on particular design specifications. In some embodiments, additionally or alternatively, an audio protector type is utilized to determine the applicable frequency ranges. For example, in some embodiments, over-the-ear audio protectors are associated with a first plurality of frequency ranges in one or more mode(s), and in-ear audio protectors are associated with a second plurality of frequency rages in one or more mode(s).

In some embodiments, a particular frequency range is processed via the audio comparison model. For example, in some embodiments, the apparatus 300 determines a dynamic frequency threshold utilized to process a particular frequency range that falls at or below the dynamic frequency threshold. In some embodiments, the apparatus 300 determine the dynamic frequency threshold based at least in part on external audio data. In some embodiments, the dynamic frequency threshold is determinable utilizing an algorithm, trained machine learning model, and/or the like. For example, in some embodiments as an energy level or loudness of external noise represented by the external audio data increases, the dynamic frequency threshold may decrease from a predetermined threshold until a particular loudness level is reached (e.g., a level at which the user-generated audio is drowned out by the loudness of the environment).

At operation 712, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that computes energy differential data. In some embodiments, the apparatus 300 computes the energy differential data by applying the comparative internal data and the comparative external data to the audio comparison model. In some embodiments, the audio comparison model includes a specially configured algorithmic, statistical, and/or machine-learning model that determines a difference between the energy level of the comparative external data and the comparative internal data. In some embodiments, the comparison is performed at each frequency range of a plurality of frequency ranges.

In some embodiments, the apparatus 300 processes the energy differential data to determine a fit result. For example, in one example context, the ideal energy differential data is 0 in a circumstance where the inverse attenuation model represents a determined best fit for a particular audio protector, such that the actual internal audio data and the estimated data derived via the inverse attenuation model represents the same energy levels. In some embodiments, the fit result indicates whether the energy differential data indicates a satisfactory fit of the audio protector. Alternatively or additionally, in some embodiments, the fit result embodies one from a candidate set of fit results (e.g., each indicating a different level of satisfactory fit). For example, the energy differential data may be compared to one or more thresholds, such as embodying acceptable range(s) within which the energy differential data may fall and/or an expected value for the energy differential data. In some embodiments, the apparatus 300 determines the external audio data and/or internal audio data indicates a satisfactory fit of the audio protector in a circumstance where the energy differential data satisfies one or more particular threshold(s). Alternatively or additionally, in some embodiments, the apparatus 300 determines the external audio data and/or internal audio data indicates a dissatisfactory fit of the audio protector in a circumstance where the energy differential data does not satisfy one or more particular threshold(s).

In some embodiments, the apparatus 300 determines whether the processed data indicates a satisfactory fit of the audio protector based at least in part on at least one warning threshold. For example, at operation 712, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that compares the energy differential data to at least one warning threshold. In some embodiments, the at least one warning threshold embodies a threshold value that, if not satisfied (e.g., exceeded in one example context), indicates that the audio protector is associated with a dissatisfactory fit to the extent that sound may harm the user's hearing. The at least one warning threshold in some embodiments represents a maximum value of the energy differential data that indicates a satisfactory fit of the audio protector. In some embodiments, the apparatus 300 expects the energy differential data to represent a value of 0 in a circumstance where the audio protector is perfectly fit. In this regard, the at least one warning threshold may indicate a maximum deviation from 0 within which a user's hearing is not determined to be sufficiently at risk of harm, such that the apparatus 300 determines the data indicates a satisfactory fit of the audio protector in a circumstance where the warning threshold is satisfied and the data indicates a dissatisfactory fit of the audio protector in a circumstance where the warning threshold is not satisfied.

At optional operation 714, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that, based at least in part on the comparison, cause outputting of a warning message. In some embodiments, the apparatus 300 causes outputting of the warning message via at least one output component associated with the audio protector. In some embodiments, the at least one output component embodies a speaker or other audio output component on or otherwise integrated into the audio protector, an interface, light, or otherwise visual output component on or otherwise integrated into the audio protector, and/or the like. In some other embodiments, the at least one output component embodies a visual output and/or audio output of a user device associated with the audio protector. For example, in some embodiments, the apparatus 300 maintains an association between a particular audio protector and a corresponding user device. Additionally or alternatively still, in some embodiments, the at least one output component embodies an emergency warning system, siren, visual alarm, or other environmental indicator within an environment around the audio protector that is usable to convey or otherwise indicate the warning message to a user within the environment.

In some embodiments, the warning message indicates an audio protector has been determined associated with a dissatisfactory fit. In some embodiments, the warning message includes audio data for outputting via the output component. Alternatively or additionally, in some embodiments, the warning message includes data for rendering to one or more output component(s), for example a display or other user interface. Alternatively or additionally still, in some embodiments, the warning message includes data utilized for activating one or more visual and/or audio indicators, for example on the audio protector or in the environment around the audio protector and/or a user.

In some embodiments, the apparatus 300 repeats the process 700 any number of times. For example, in some embodiments, the apparatus 300 continuously performs the process 700. In this regard, for example, some such embodiments may continuously perform the process 700 to warn a user when a fit of an audio protector worn by the user is or becomes dissatisfactory. In this regard such embodiments are capable of warning a user-real time where audio signals indicate a dissatisfactory fit posing a risk to a user's hearing. Alternatively or additionally, in some embodiments, the apparatus 300 initiates the process 700 upon power up or a first initiation by a user indicating a request to perform the automatic fit testing.

Figure 8:
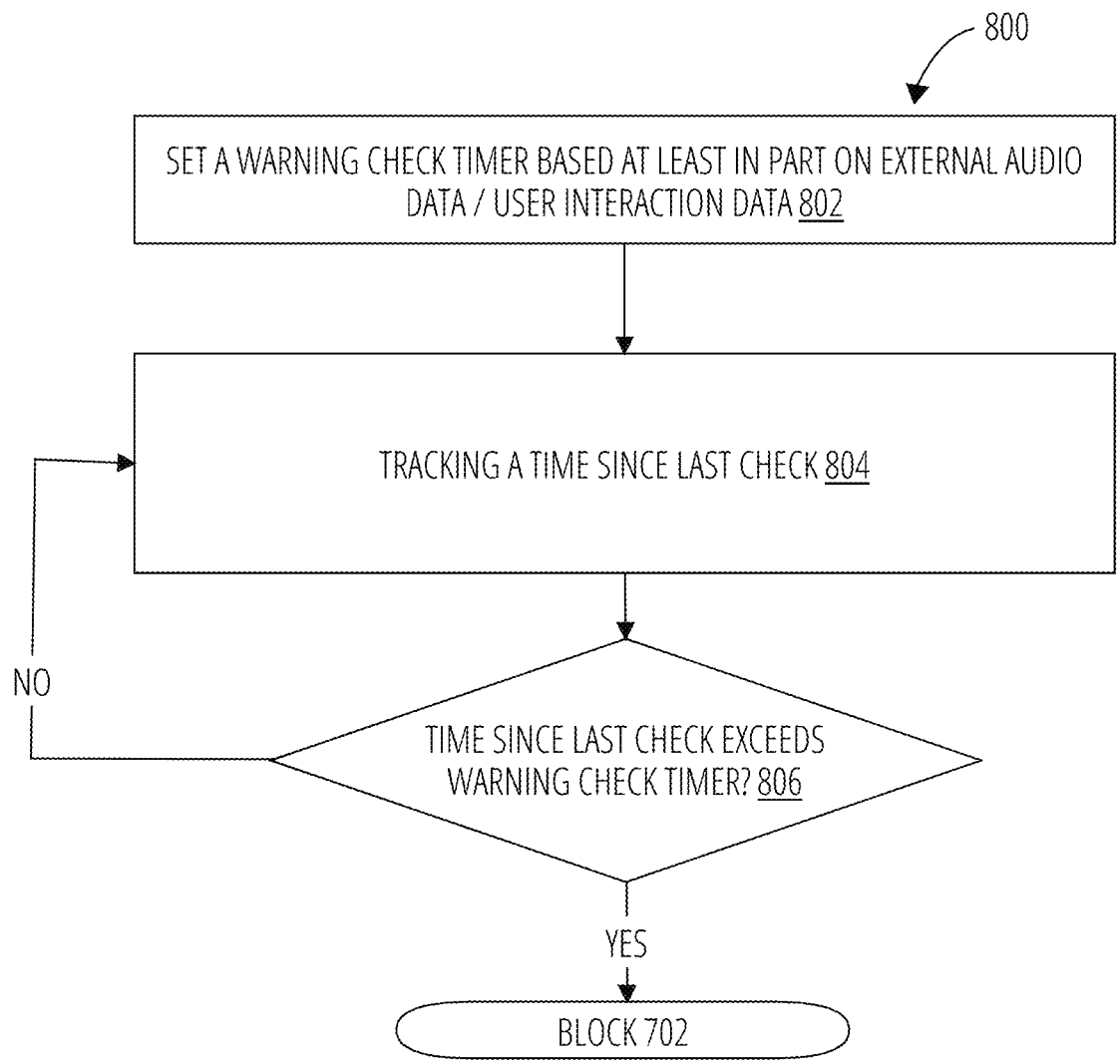
FIG. 8 illustrates a flowchart depicting operations of an example process for initiating a fit test in accordance with at least one embodiment of the present disclosure.

FIG. 8 illustrates a flowchart depicting operations of an example process for initiating a fit test in accordance with at least one embodiment of the present disclosure. Specifically, FIG. 8 depicts operations of an example process 800. In some embodiments, the process 800 is embodied by computer program code stored on a non-transitory computer-readable storage medium of a computer program product configured for execution to perform the process as depicted and described. Alternatively or additionally, in some embodiments, the process 800 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one user device, warning system, external output component, and/or the like. For purposes of simplifying the description, the process 800 is described as performed by and from the perspective of the apparatus 300.

In some embodiments, the process 800 is embodied by computer program code stored on a non-transitory computer-readable storage medium of a computer program product configured for execution to perform the process as depicted and described. Alternatively or additionally, in some embodiments, the process 800 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one apparatus, at least one sensor associated with the at least one apparatus, at least one end-user computing device, and/or in some embodiments an optional external control system. For purposes of simplifying the description, the process 800 is described as performed by and from the perspective of the apparatus 300.

The process 800 beings at operation 802. In some embodiments, the process 800 begins after one or more operations depicted and/or described with respect to any one of the other processes described herein. In this regard, some or all of the process 800 may replace or supplement one or more blocks depicted and/or described with respect to any of the processes described herein. Upon completion of the process 800, the flow of operations may terminate. Additionally or alternatively, as depicted, upon completion of the process 800 in some embodiments, flow may return to one or more operation(s) of another process, such as the operation 702. It will be appreciated that, in some embodiments, the process 800 embodies a sub-process of one or more other process(es) depicted and/or described herein, for example the process 700.

At operation 802, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that sets a warning check timer based at least in part on external audio data and/or user interaction data. In some embodiments, the warning check timer embodies a time interval between performance of one or more process(es) for automatic fit testing, for example as described with respect to FIG. 7. For example, in some embodiments, the warning check timer is set based on an energy level associated with the external audio data. In some such embodiments, the apparatus 200 automatically sets the warning check timer such that a higher energy level (e.g., indicating louder sound) determined for the external audio data is associated with a longer warning check timer. For example, in some embodiments, the apparatus 300 maintains a plurality of energy level ranges, each energy level range corresponding to a particular warning check timer. In this regard, in a circumstance where the apparatus 300 determines that the external audio data is associated with a particular energy level, the apparatus 300 may set the warning check timer to a particular value based at least in part on the particular warning check timer corresponding to the range within which the particular energy level falls.

Alternatively or additionally, in some embodiments, the apparatus 300 sets the warning check timer based at least in part on user interaction data. For example, in some embodiments, the user interaction data embodies a user inputted data value for setting the warning check timer. The user may set the warning check timer to any desired value, a predetermined value, a value determined based at least in part on the one or more characteristic(s) of the audio protector, and/or the like.

At operation 804, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that tracks a time since last check. In some embodiments, the apparatus 300 updates the time since last check based on a current time. Alternatively or additionally, in some embodiments, the apparatus 300 updates the time since last check for each frame or clock cycle of the process during execution. In this regard, the time since last check may continue to be updated as time progresses to represent the amount of time since the particular timestamp represented by the time since last check.

At operation 806, the apparatus 300 determines whether the time since last check exceeds the warning check timer. The apparatus 300 may perform the determination by comparing the time since last check with the warning check timer. In some circumstances, the apparatus 300 determines the time since last check exceeds the warning check timer in a circumstance where the apparatus 300 determines that the comparison indicates that the time since last check exceeds the warning check timer.

In some embodiments, in a circumstance where the apparatus 300 determines that the time since the last check does not exceed the warning check timer at operation 806, flow returns to operation 804. In this regard, the apparatus 300 may continue to track the time since last check until the determination at block 806 is satisfied. Alternatively or additionally, in a circumstance where the apparatus 300 determines that the time since the last check exceeds the warning check timer at operation 806, the flow may continue to perform one or more process(es) for automatic fit testing, for example by proceeding to the process 700. In some embodiments, the process 800 embodies a cycle that is repeated continuously, for example so long as the apparatus 300 is activated or otherwise powered on.

Figure 9:
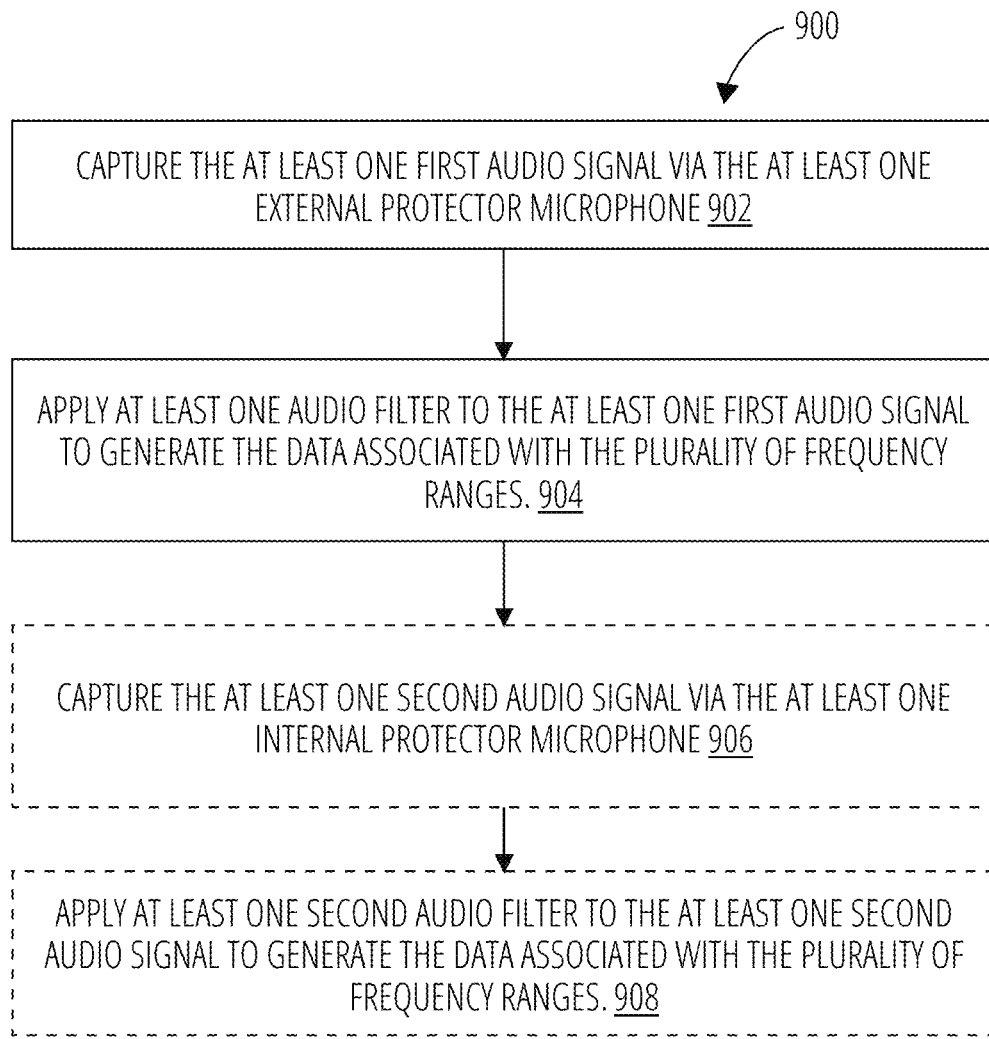
FIG. 9 illustrates a flowchart depicting operations of an example process for capturing audio signals for processing as part of a fit test in accordance with at least one embodiment of the present disclosure.

FIG. 9 illustrates a flowchart depicting operations of an example process for capturing audio signals for processing as part of a fit test in accordance with at least one embodiment of the present disclosure. Specifically, FIG. 9 depicts operations of an example process 900. In some embodiments, the process 900 is embodied by computer program code stored on a non-transitory computer-readable storage medium of a computer program product configured for execution to perform the process as depicted and described. Alternatively or additionally, in some embodiments, the process 900 is performed by one or more specially configured computing devices, such as the apparatus 300 alone or in communication with one or more other component(s), device(s), system(s), and/or the like.

In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one user device, warning system, external output component, and/or the like. For purposes of simplifying the description, the process 900 is described as performed by and from the perspective of the apparatus 300.

In some embodiments, the process 900 is embodied by computer program code stored on a non-transitory computer-readable storage medium of a computer program product configured for execution to perform the process as depicted and described. Alternatively or additionally, in some embodiments, the process 900 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one apparatus, at least one sensor associated with the at least one apparatus, at least one end-user computing device, and/or in some embodiments an optional external control system. For purposes of simplifying the description, the process 900 is described as performed by and from the perspective of the apparatus 300.

The process 900 beings at operation 902. In some embodiments, the process 900 begins after one or more operations depicted and/or described with respect to any one of the other processes described herein. In this regard, some or all of the process 900 may replace or supplement one or more blocks depicted and/or described with respect to any of the processes described herein, for example operations 702 and/or 704 as depicted and described. Upon completion of the process 900, the flow of operations may terminate. Additionally or alternatively, as depicted, upon completion of the process 900 in some embodiments, flow may return to one or more operation(s) of another process, such as the operation 704 or 706. It will be appreciated that, in some embodiments, the process 900 embodies a sub-process of one or more other process(es) depicted and/or described herein, for example the process 700.

At operation 902, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that captures the at least one first audio signal via the at least one external protector microphone. The at least one first audio signal may represent audio energy levels of sound captured from an environment without attenuation by components of the audio protector. For example, in this regard, the at least one first audio signal may correspond to the audio signals that would affect the user's hearing without wearing the audio protector.

At operation 904, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that applies at least one audio filter to the at least one first audio signal to generate the data associated with the plurality of frequency ranges. Alternatively or additionally, in some embodiments, the apparatus 300 applies the at least one audio filter to data derived from the first audio signal, for example via an inverse attenuation model. In some embodiments, the at least one audio filter is predetermined or otherwise maintained by the apparatus 300. The at least one audio filter may partition the at least one first audio signal, and/or data derived therefrom, into a plurality of data portions that correspond to particular frequency bands. In this regard, the resulting processed external audio data, for example, may include indications of the various data portions associated with their corresponding frequency band. Alternatively or additionally, in some embodiments, the at least one audio filter blocks or otherwise filters out one or more particular frequencies and/or frequency bands from the audio signal, or data derived therefrom, to produce corresponding processed data. In this regard, the resulting data associated with the plurality of frequency ranges may include data representing the remaining, non-filtered portions of the at least one first audio signal or data derived therefrom.

At optional operation 906, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that captures the at least one second audio signal via at least one internal protector microphone. The at least one second audio signal may represent audio energy levels of sound captured from within an internal portion of the audio protector after attenuation by component(s) of the audio protector (e.g., one or more sound dampener(s)). For example, in this regard, the at least one second audio signal may correspond to the attenuated audio signals that are diminished before reaching the user's ear while wearing the audio protector. The at least one second audio signal may embody or be utilized to derive internal audio data for further processing.

At operation 908, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that applies at least one second audio filter to the at least one second audio signal to generate the data associated with the plurality of frequency ranges. In some embodiments, the data represents a filtered version of the internal audio signal and/or data processed therefrom (e.g., to remove hear-through effects). In some embodiments, the at least one second audio filter is predetermined or otherwise maintained by the apparatus 300. In some embodiments, the at least one second audio filter embody the same audio filter(s) applied to the first audio signals described herein. The at least one second audio filter may partition the at least one second audio signal, or data derived therefrom, into a plurality of data portions that correspond to particular frequency bands. In this regard, the resulting processed data, for example, may include indications of the various data portions associated with their corresponding frequency band. Alternatively or additionally, in some embodiments, the at least one second audio filter blocks or otherwise filters out one or more particular frequencies and/or frequency bands from the audio signal to produce corresponding processed data. In this regard, the resulting data associated with the plurality of frequency ranges may include data representing the remaining, non-filtered portions of the at least one second audio signal.

Figure 10:
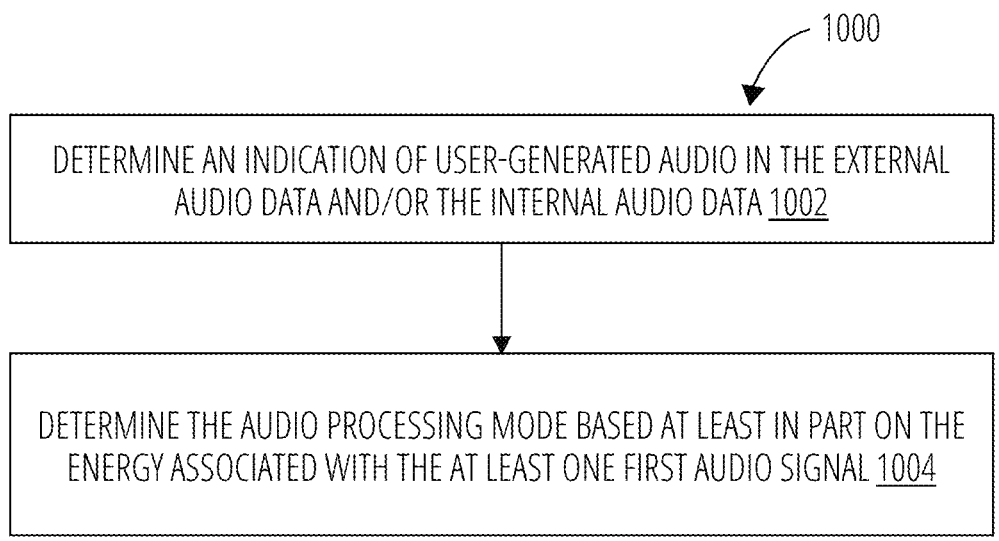
FIG. 10 illustrates a flowchart depicting operations of an example process for determining an audio processing mode in accordance with at least one embodiment of the present disclosure.

FIG. 10 illustrates a flowchart depicting operations of an example process for determining an audio processing mode in accordance with at least one embodiment of the present disclosure. Specifically, FIG. 10 depicts operations of an example process 1000. In some embodiments, the process 1000 is embodied by computer program code stored on a non-transitory computer-readable storage medium of a computer program product configured for execution to perform the process as depicted and described. Alternatively or additionally, in some embodiments, the process 1000 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one user device, warning system, external output component, and/or the like. For purposes of simplifying the description, the process 1000 is described as performed by and from the perspective of the apparatus 300.

In some embodiments, the process 1000 is embodied by computer program code stored on a non-transitory computer-readable storage medium of a computer program product configured for execution to perform the process as depicted and described. Alternatively or additionally, in some embodiments, the process 900 is performed by one or more specially configured computing devices, such as the apparatus 300 alone or in communication with one or more other component(s), device(s), system(s), and/or the like. In this regard, in some such embodiments, the apparatus 300 is specially configured by computer-coded instructions (e.g., computer program instructions) stored thereon, for example in the memory 304 and/or another component depicted and/or described herein and/or otherwise accessible to the apparatus 300, for performing the operations as depicted and described. In some embodiments, the apparatus 300 is in communication with one or more external apparatus(es), system(s), device(s), and/or the like, to perform one or more of the operations as depicted and described. For example, the apparatus 300 in some embodiments is in communication with at least one apparatus, at least one sensor associated with the at least one apparatus, at least one end-user computing device, and/or in some embodiments an optional external control system. For purposes of simplifying the description, the process 1000 is described as performed by and from the perspective of the apparatus 300.

The process 1000 beings at operation 1002. In some embodiments, the process 1000 begins after one or more operations depicted and/or described with respect to any one of the other processes described herein, for example operation 706 as depicted and described. In this regard, some or all of the process 1000 may replace or supplement one or more blocks depicted and/or described with respect to any of the processes described herein, for example operation 706 as depicted and described. Upon completion of the process 1000, the flow of operations may terminate. Additionally or alternatively, as depicted, upon completion of the process 900 in some embodiments, flow may return to one or more operation(s) of another process, such as the operation 710. It will be appreciated that, in some embodiments, the process 1000 embodies a sub-process of one or more other process(es) depicted and/or described herein, for example the process 700.

At operation 1002, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that determines an indication of user-generated audio in the external audio data and/or internal audio data. In some embodiments, the apparatus 300 applies the external audio data and/or the internal audio data to a user-generated audio detection model. For example, in some embodiments the user-generated audio detection model is trained to detect particular keywords, tones, and/or the like. The user-generated audio detection model in some embodiments includes an algorithmic, statistical, and/or machine-learning model specially trained to detect indications of user-generated audio from captured audio data. In some embodiments, the user-generated audio detection model detects the user-generated audio from either the external audio data or the internal audio data.

At operation 1004, the apparatus 300 includes means such as captured audio manipulation circuitry 310, fit determination circuitry 312, warning generation circuitry 314, communications circuitry 308, input/output circuitry 306, processor 302, and/or the like, or a combination thereof, that determine the audio processing mode based at least in part on the energy associated with the at least one first audio signal. In some embodiments, the apparatus 300 determines whether the energy associated with the at least one first audio signal falls within a particular range. For example, the apparatus 300 may determine whether an energy level associated with the first audio signal falls below a particular threshold or above a particular threshold. Additionally or alternatively, in some embodiments, the apparatus 300 may determine whether an energy level associated with the first audio signal falls below a first threshold, between the first threshold and a second threshold, or above the second threshold. Alternatively or additionally still, in some embodiments the apparatus 300 determines the audio processing mode based at least in part on the determination of whether user-generated audio was present in one or more portions of audio data, as described herein with respect to operation 1002 for example, in addition to being based on the energy associated with the at least one first audio signal. In some embodiments, the apparatus 300 determines the audio processing mode utilizing a mode table stored by and/or otherwise maintained via the apparatus 300. In this regard, the particular identified audio processing mode may be selected based on the current environmental and/or audio circumstances indicated by the data as actually captured, for example to enable corresponding model(s) to be identified and used for accurately processing the data as captured in real-time.

Example Data Graphs of the Disclosure

Example data graphs representing data values for particular characteristics of audio signals captured in accordance with at least one embodiment of the present disclosure will now be discussed. In particular, the depicted and described data graphs depicts such particular characteristics (e.g., energy levels) of such a signals at various frequencies of frequency ranges that define particular frequency bands. The characteristics are depicted and described for different types of fit of a particular audio protector in accordance with the present disclosure. For example, in some embodiments, the data points represent data values captured in testing conditions for particular fits and environmental circumstances, and/or averages or other values derived from such captured testing data. In this regard, the depicted and described data graphs may be utilized in some embodiments to define, generate, and/or train particular model(s), for example at least an inverse attenuation model, based on a particular fit. For example, in one example context, the data graphs may be utilized to configure the inverse attenuation model to represent the effects of a satisfactory or "good" fit of an audio protector on one or more wearer(s). In some embodiments, the inverse attenuation model embodies one or more machine learning model(s) trained on such data and/or additional data, for example user-generated audio data for different voice(s), sound(s), types of user(s) (e.g., with different biographical characteristics, such as male and female, old or young, and/or the like), and/or the like. In this regard, any distinction(s) between different fit result(s) (e.g., a good fit and a bad fit, or any gradation level(s) for good fit and bad fit) may be derivable into an inverse attenuation model based at least in part on the differences in audio data represented for the various frequency ranges in a particular graph.

Figure 11:
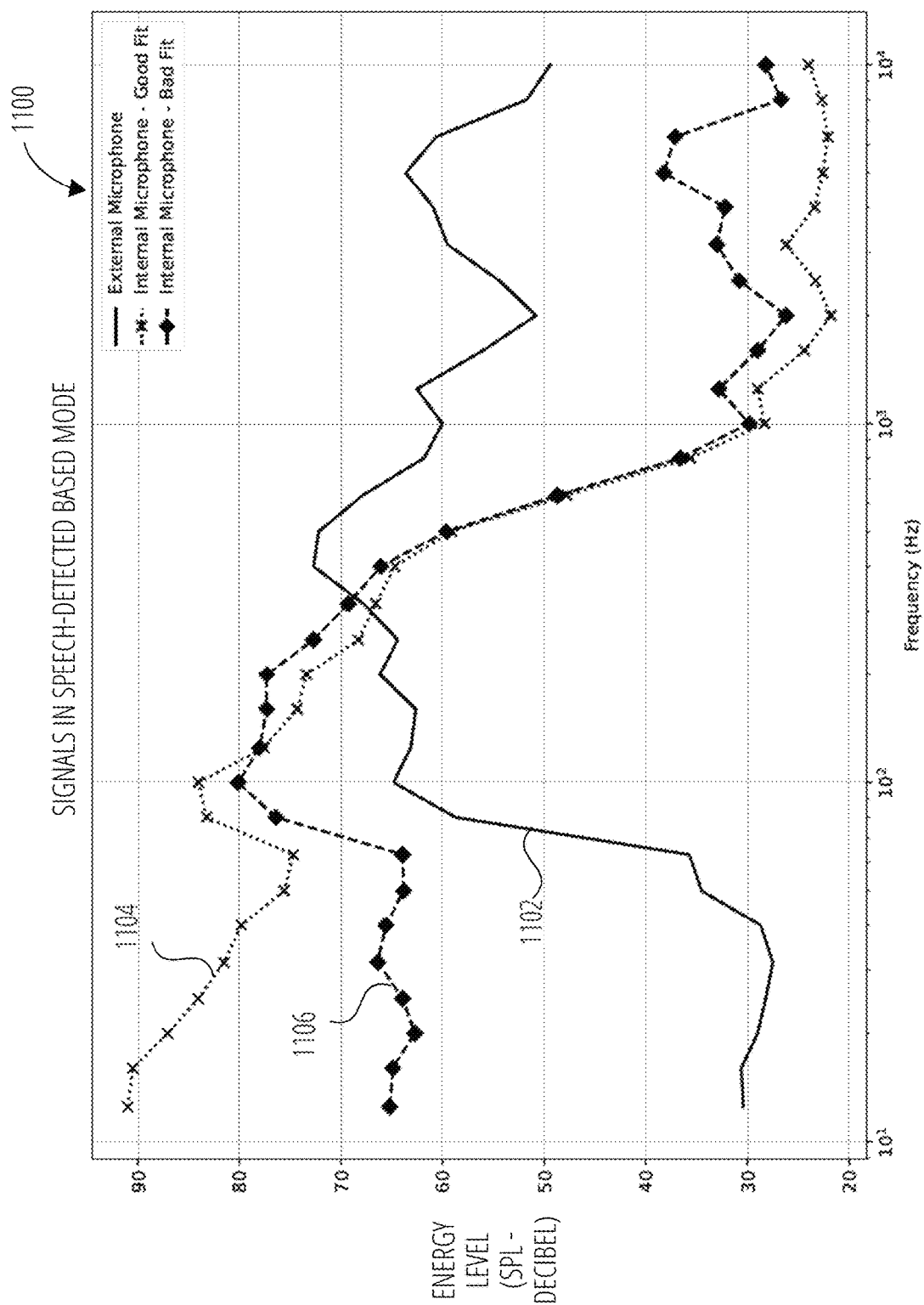
FIG. 11 illustrates a graph of various audio data as part of an automatic audio fit test in a mode where user-generated audio is detected and considered in accordance with at least one embodiment of the present disclosure.

FIG. 11 illustrates a graph of various audio data as part of an automatic audio fit test in a mode where user-generated audio is detected and considered in accordance with at least one embodiment of the present disclosure. Specifically, FIG. 11 depicts an example graph 1100. The graph 1100 represents data values for various example audio data representing signals captured via an example apparatus embodying an over-the-ear audio protector specially configured for performing an automatic fit testing process in accordance with the present disclosure. The graph 1100 corresponds to a circumstance where user-generated audio is present within the environment, for example where a user wearing the audio protector is talking, eating, or otherwise generating sounds that may be picked up by the internal and/or external audio protector microphones and represented in the corresponding data. For example, in some embodiments, such user-generated data is detected based on processing particular frequency ranges of the internal audio data and/or external audio data.

As illustrated, the graph 1100 includes various plots representing data values for audio data captured in different microphones in different fit circumstances by a specially configured audio protector, for example embodied by the apparatus 300. Specifically, graph 1100 includes an external audio data plot 1102. The external audio data plot 1102 includes various data points based on data values of external audio data captured by one or more external protector microphone(s). As depicted, the external audio data plot 1102 includes the energy level (e.g., a sound pressure level measured in decibels) of such data depicted along the y-axis of different frequency ranges (e.g., a frequency measured in hertz) depicted along the x-axis. In this regard, the external audio data plot 1102 may represent the environmental signals (e.g., a volume of audio) at different frequency ranges before such signals are affected by component(s) of the audio protector.

The graph 1100 further includes a good fit internal audio data plot 1104. The good fit internal audio data plot 1104 includes data points based on data values of internal audio data captured by one or more internal protector microphone(s) in a circumstance where an audio protector is worn with a good (e.g., at or above satisfactory) fit. As depicted, the good fit internal audio data plot 1104 similarly includes the energy level of such data depicted along the y-axis of different frequency ranges depicted along the x-axis. As indicated by the good fit internal audio data plot 1104, in a circumstance where the audio protector is worn with a good fit, the corresponding data indicates that lower frequencies are associated with significantly higher energy levels, for example in frequencies up to 300 Hz, than the corresponding external audio data of the external audio data plot 1102. In some embodiments, such lower frequencies may be the only processed frequencies in some such modes where user-generated audio is detected.

The graph 1100 further includes a bad fit internal audio data plot 1106. The bad fit internal audio data plot 1106 includes data points based on data values of internal audio data captured by one or more internal protector microphone(s) in a circumstance where an audio protector is worn with a bad (e.g., dissatisfactory or otherwise below satisfactory) fit. As depicted, the bad fit internal audio data plot 1106 similarly includes the energy level of such data depicted along the y-axis of different frequency ranges depicted along the x-axis. As indicated by the bad fit internal audio data plot 1106, in a circumstance where the audio protector is worn with a bad fit, the corresponding data indicates that the lower frequencies are associated with lower energy levels than the corresponding good fit internal audio data plot 1104.

In some embodiments, particular frequency ranges are associated with higher energy levels in circumstances where a good fit is represented and user-generated audio is detected. In this regard, the good fit of the audio protector forms a closed acoustic system that "traps" audio signals within such that audio signals reach the internal protector microphone(s) with a higher energy level than a corresponding bad fit, in which such audio signals would "escape" the closed acoustic system via any leaks causing the bad fit. Such increase in frequency ranges may correspond to bone conduction from the user making the user-generated audio sounds. Such bone conduction may particularly cause higher acoustical energy levels in lower frequency ranges dependent on the type and/or frequency of user-generated audio (e.g., based on the pitch of a user's voice where the user-generated audio represents user speech). The air in the cavity defined by the closed acoustic system may be excited by such vibrations directly, for example from the user's vocal chords. In this regard, the peak energy level observed for a bad fit may fall considerably compared to the peak energy level for a good fit at such frequency range(s). Such distinctions may be particularly present in circumstances where the internal portion defines a particularly low volume space.

Such excitations in particular frequency ranges may be depicted for a good fit of an audio protector even in circumstances in which the external noise level is particularly high. In this regard, such distinctions between energy levels at such frequency range(s) may be utilized to identify good fit versus bad fit in both environments of particularly low ambient noise levels, moderate ambient noise levels, and/or ambient noise levels. Such distinctions between modes for example further reduce and/or eliminate misidentifying the increase in energy at particular frequency range(s) (e.g., at low frequency ranges) as a leak instead of user-generated noise.

Figure 12:
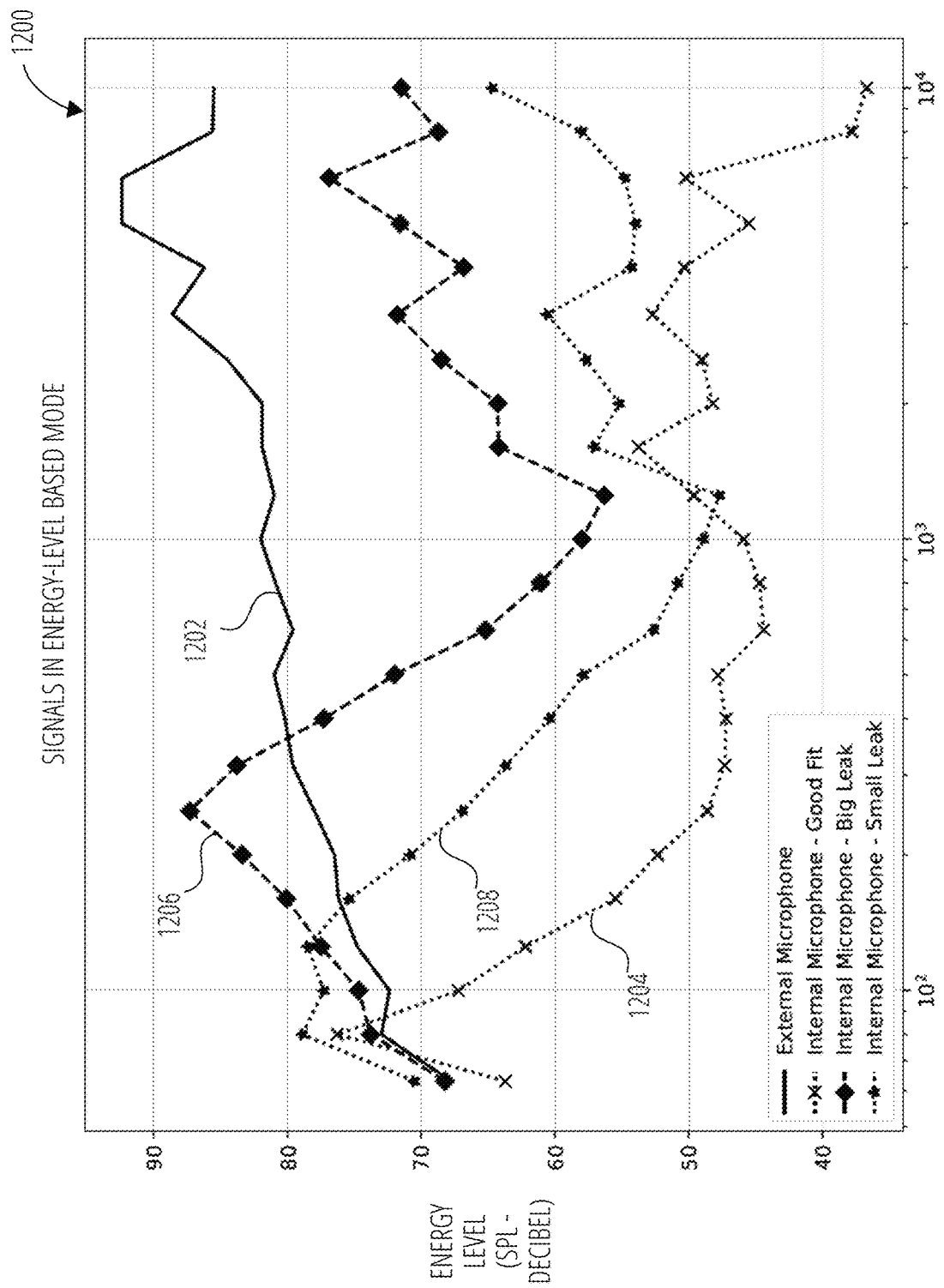
FIG. 12 illustrates a graph of various audio data as part of an automatic audio fit test in a mode where user-generated audio is not detected or is not considered in accordance with at least one embodiment of the present disclosure.

FIG. 12 illustrates a graph of various audio data as part of an automatic audio fit test in a mode where user-generated audio is not detected or is not considered in accordance with at least one embodiment of the present disclosure. Specifically, FIG. 12 depicts an example graph 1200. The graph 1200 represents data values for various example audio data representing signals captured via an example apparatus embodying an over-the-ear audio protector specially configured for performing an automatic fit testing process in accordance with the present disclosure. The graph 1200 corresponds to a circumstance where user-generated audio is not within the environment, for example where a user wearing the audio protector is not generating sounds that may be picked up by the internal and/or external audio protector microphones and/or such sounds are drowned out by environmental sounds.

As illustrated, the graph 1200 includes various plots representing data values for audio data captured in different microphones in different fit circumstances by a specially configured audio protector, for example embodied by the apparatus 300. Specifically, graph 1200 includes an external audio data plot 1202. Similarly to the external audio data plot 1102, the external audio data plot 1202 includes various data points based on data values of external audio data captured by one or more external protector microphone(s) of an audio protector. As depicted, the external audio data plot 1202 includes the energy level (e.g., a sound pressure level measured in decibels) of such data depicted along the y-axis of different frequency ranges (e.g., a frequency measured in hertz) depicted along the x-axis. In this regard, the external audio data plot 1202 may represent the environmental signals (e.g., a volume of audio) at different frequency ranges before such signals are affected by the component(s)m of the audio protector.

The graph 1200 further includes data plots corresponding to three different fit results, specifically a good fit result, a small leak fit result, and a big leak fit result. In some embodiments, the good fit result and the small leak fit result correspond to a satisfactory fit, and the big leak fit result corresponds to a dissatisfactory fit. Alternatively or additionally, in some embodiments a warning message is generated and/or output for only the big leak fit result, or for both the big leak fit result and the small leak fit result.

The graph 1200 includes a good fit internal audio data plot 1204. The good fit internal audio data plot 1204 includes data points based on data values of internal audio data captured by one or more internal protector microphone(s) in a circumstance where an audio protector is worn with a good (e.g., at or above satisfactory) fit. As depicted, the good fit internal audio data plot 1204 similarly includes the energy level of such data depicted along the y-axis of different frequency ranges depicted along the x-axis. As indicated by the good fit internal audio data plot 1204, in a circumstance where the audio protector is worn with a good fit, the corresponding data indicates that higher frequencies are associated with significantly lower energy levels than the corresponding external audio data of the external audio data plot 1202 (e.g., indicating that the audio protector is blocking such frequencies from reaching the user internal protector microphone(s) and thereby affecting the user's hearing). Additionally, in a circumstance where the audio protector is worn with a good fit, relatively low energy levels are present at lower frequencies, resulting in higher differences between energy levels for internal audio data for and energy levels for external audio data. In some embodiments, various frequency ranges may be processed independently, for example to capture the distinction in data level differences between a good fit and a bad fit for a low-pass frequency range and a high-pass frequency range.

The graph 1200 further includes a small leak internal audio data plot 1208. The small leak internal audio data plot 1208 includes data points based on data values of internal audio data captured by one or more internal protector microphone(s) in a circumstance where an audio protector is worn with a fit having small leaks between sound dampener(s) or other components and the wearing user. As depicted, the small leak internal audio data plot 1208 similarly includes the energy level of such data depicted along the y-axis of different frequency ranges depicted along the x-axis. As indicated by the small leak internal audio data plot 1208 in a circumstance where the audio protector is worn with small gaps that allow some audio signals to leak through to the internal portion of the audio protector, the corresponding data indicates that several frequency ranges (including various lower frequencies and various higher frequencies) are associated with lower energy levels than the corresponding external audio data plot 1202 but at higher energy levels than the corresponding good fit internal audio data plot 1204.

Further still, the graph 1200 further includes a big leak internal audio data plot 1206 The big leak internal audio data plot 1206 includes data points based on data values of internal audio data captured by one or more internal protector microphone(s) in a circumstance where an audio protector is worn with a fit having large leaks between sound dampener(s) or other components and the wearing user. As depicted, the big leak internal audio data plot 1206 similarly includes the energy level of such data depicted along the y-axis of different frequency ranges depicted along the x-axis. As indicated by the big leak internal audio data plot 1206, in a circumstance where the audio protector is worn with large gaps that allow many audio signals to leak through to the internal portion of the audio protector without significant attenuation, the corresponding data indicates that several frequency ranges (including various lower frequencies and various higher frequencies are associated with lower energy levels than the corresponding external audio data plot 1202, but at higher energy levels than both the corresponding small leak fit internal audio data plot 1208 and the good fit internal audio data plot 1204. In this regard, it should be appreciated that data may be captured corresponding to any number of different fit results.

As depicted, in some circumstances, the energy levels associated with internal audio data in a circumstance where the audio protector is fit with a big leak may exceed the energy levels associated with the external audio data. For example, as illustrated in FIG. 12, the energy levels associated with the big leak internal audio data plot 1206 exceed the energy levels associated with the external audio data plot 1202 for the frequency range of approximately 200-300 Hz. In this regard, such an increase in energy levels at any frequency range in some modes, and/or at particular frequency range(s) above a certain cutoff may represent significant amounts of unattenuated audio signals are leaking into the internal potion of the audio protector, thus indicating a big leak and a bad fit.

In some embodiments, the data plots captured corresponding to particular fit result(s) is/are utilized to specially train and/or otherwise configure one or more model(s). For example, in some embodiments, the data values corresponding to the external audio data plots and/or internal audio data plots depicted with respect to FIG. 11 and/or FIG. 12 may be utilized to train one or more model(s) that determine a fit result from subsequently captured and/or real-time data. For example, model(s) such as an audio comparison model, may be specially trained to determine what energy differential data (e.g., determined based on the difference between the two plots at each frequency or frequency range) indicates different fit results. Alternatively or additionally, in some embodiments, such plots are utilized to specially configure a particular algorithm that determines a fit result for real-time or subsequently captured data based on the energy differential data determinable from the difference between the external audio data plot and internal audio data plots for different fit results. For example, in some embodiments, the apparatus 300 is configured to utilize a particular model that is trained or otherwise configured based on a training data set embodied by or derived from the internal audio data and/or external audio data utilized to generate one or more plots, for example those as depicted and described with respect to FIGS. 11 and 12.

CONCLUSION

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:
   receiving external audio data representing first energy associated with at least one first audio signal captured via at least one external protector microphone of an audio protector;
   receiving internal audio data representing second energy associated with at least one second audio signal captured via at least one internal protector microphone of the audio protector;
   generating comparative external data by at least applying the external audio data to an inverse attenuation model;
   generating comparative internal data based at least in part on the internal audio data;
   identifying an audio processing mode based at least in part on the external audio data and/or the internal audio data, the audio processing mode associated with an audio comparison model;
   computing energy differential data by applying the comparative internal data and the comparative external data to the audio comparison model;
   determining a fit result based at least in part on the energy differential data;
   applying the internal audio data to an inverse hear-through model to generate updated internal audio data; and
   generating the comparative internal data based at least in part on the updated internal audio data.

2. The computer-implemented method of claim 1, wherein generating the comparative internal data further comprises applying a first filtering model to the internal audio data, and wherein generating the comparative external data further comprises applying a second filtering model to the external audio data.

3. The computer-implemented method of claim 1, wherein the audio comparison model compares the comparative internal data and the comparative external data at each frequency band of a plurality of frequency bands.

4. The computer-implemented method of claim 1, the computer-implemented method further comprising:

based at least in part on the comparison, causing outputting of a warning message via at least one output component associated with the audio protector.

5. The computer-implemented method of claim 1, the computer-implemented method further comprising:
setting a warning check timer based at least in part on the external audio data; and
tracking a time since last check, wherein the remaining steps of the computer-implemented method of claim 1 are performed in a circumstance where the time since last check is determined to exceed the warning check timer.

6. The computer-implemented method of claim 1, the computer-implemented method further comprising:
outputting a warning message via at least one speaker of the audio protector.

7. The computer-implemented method of claim 1, the computer-implemented method further comprising:
outputting a warning message via at least one output component associated with the audio protector,
wherein the warning message is output at a first rate in a circumstance where the first energy associated with the at least one first audio signal is below a first energy threshold, and
wherein the warning message is output at a second rate in a circumstance where the first energy associated with the at least one first audio signal is above the first energy threshold, wherein the second rate is faster than the first rate.

8. The computer-implemented method of claim 1, the computer-implemented method further comprising:
setting a warning check timer based at least in part on user interaction data; and
tracking a time since last check, wherein the remaining steps of the computer-implemented method of claim 1 are performed in a circumstance where the time since last check is determined to exceed the warning check timer.

9. The computer-implemented method of claim 1, wherein receiving the external audio data comprises:
capturing the at least one first audio signal via the at least one external protector microphone.

10. The computer-implemented method of claim 1, wherein receiving the internal audio data comprises:
capturing the at least one second audio signal via the at least one internal protector microphone.

11. The computer-implemented method of claim 1, wherein the audio processing mode is selected from a plurality of candidate modes, the plurality of candidate modes comprising:
a first mode selected in a circumstance where the external audio data and/or the internal audio data indicates a quiet level associated with the audio protector without user-generated audio,
a second mode selected in a circumstance where the external audio data and/or the internal audio data indicates the quiet level associated with the audio protector with the user-generated audio,
a third mode selected in a circumstance where the external audio data and/or the internal audio data indicates a moderately loud level associated with the audio protector without the user-generated audio,
a fourth mode selected in a circumstance where the external audio data and/or the internal audio data indicates the moderately loud level associated with the audio protector with the user-generated audio, and
a fifth mode selected in a circumstance where the external audio data and/or the internal audio data indicates a significantly loud level associated with the audio protector with or without the user-generated audio.

12. The computer-implemented method of claim 1, wherein identifying the audio processing mode based at least in part on the external audio data and/or the internal audio data comprises:
determining an indication of user-generated audio in the external audio data and/or the internal audio data; and
determining the audio processing mode based at least in part on the first energy associated with the at least one first audio signal.

13. The computer-implemented method of claim 1, wherein determining the fit result comprises:
comparing the energy differential data to at least one warning threshold.

14. The computer-implemented method of claim 1, wherein generating the comparative internal data based at least in part on the updated internal audio data comprises:
applying the updated internal audio data to a filtering model to generate the comparative internal data.

15. An audio protector comprising:
at least one external protector microphone positioned on an external portion of the audio protector;
at least one internal protector microphone positioned on an internal portion of the audio protector;
at least one sound dampener positioned between the external portion of the audio protector and the internal portion of the audio protector; and
at least one processor that is caused to:
receive external audio data representing first energy associated with at least one first audio signal captured via the at least one external protector microphone of the audio protector;
receive internal audio data representing second energy associated with at least one second audio signal captured via the at least one internal protector microphone of the audio protector;
generate comparative external data by at least applying the internal audio data to an inverse attenuation model;
generate comparative internal data based at least in part on the internal audio data;
identify an audio processing mode based at least in part on the external audio data and/or the internal audio data, the audio processing mode associated with an audio comparison model;
compute energy differential data by applying the comparative internal data and the comparative external data to the audio comparison model;
determine a fit result based at least in part on the energy differential data;
apply the internal audio data to an inverse hear-through model to generate updated internal audio data; and
generate the comparative internal data based at least in part on the updated internal audio data.

16. The audio protector of claim 15, the audio protector further comprising:
at least one speaker,
wherein the at least one processor is further caused to at least:
based at least in part on the comparison, cause outputting of a warning message via the at least one speaker.

17. The audio protector of claim 15, the audio protector further comprising:

at least one visual indicator, wherein the at least one processor is further caused to at least:
based at least in part on the comparison, cause outputting of a warning message via the at least one visual indicator.

18. The audio protector of claim 15, the at least one processor further configured to select the audio processing mode is selected from a plurality of candidate modes, the plurality of candidate modes comprising:
a first mode selected in a circumstance where the external audio data and/or the internal audio data indicates a quiet level associated with the audio protector without user-generated audio,
a second mode selected in a circumstance where the external audio data and/or the internal audio data indicates the quiet level associated with the audio protector with the user-generated audio,
a third mode selected in a circumstance where the external audio data and/or the internal audio data indicates a moderately loud level associated with the audio protector without the user-generated audio,
a fourth mode selected in a circumstance where the external audio data and/or the internal audio data indicates the moderately loud level associated with the audio protector with the user-generated audio, and
a fifth mode selected in a circumstance where the external audio data and/or the internal audio data indicates a significantly loud level associated with the audio protector with or without the user-generated audio.

19. A computer program product comprising at least one non-transitory computer-readable storage medium having computer program code stored thereon that, in execution with at least one processor configure the computer program product for:
receiving external audio data representing first energy associated with at least one first audio signal captured via at least one external protector microphone of an audio protector;
receiving internal audio data representing second energy associated with at least one second audio signal captured via at least one internal protector microphone of the audio protector;
generating comparative external data by at least applying the external audio data to an inverse attenuation model;
generating comparative internal data based at least in part on the internal audio data;
identifying an audio processing mode based at least in part on the external audio data and/or the internal audio data, the audio processing mode associated with an audio comparison model;
computing energy differential data by applying the comparative internal data and the comparative external data to the audio comparison model;
determining a fit result based at least in part on the energy differential data;
applying the internal audio data to an inverse hear-through model to generate updated internal audio data; and
generating the comparative internal data based at least in part on the updated internal audio data.

\* \* \* \* \*